United States Patent
Aissaoui et al.

(10) Patent No.: US 7,192,950 B2
(45) Date of Patent: Mar. 20, 2007

(54) BENZAZEPINES AND RELATED HETEROCYCLIC DERIVATIVES WHICH ARE USEFUL AS OREXIN RECEPTOR ANTAGONISTS

(75) Inventors: Hamed Aissaoui, Wittenheim (FR); Martine Clozel, Binningen (CH); Thomas Weller, Binningen (CH); Ralf Koberstein, Lörrach (DE); Thierry Sifferlen, Guewenheim (FR); Walter Fischli, Allschwil (CH)

(73) Assignee: Actelion Pharmaceuticals, Ltd. (CH)

( * ) Notice: Subject to any disclaimer, the term of this patent is extended or adjusted under 35 U.S.C. 154(b) by 296 days.

(21) Appl. No.: 10/450,420

(22) PCT Filed: Dec. 19, 2001

(86) PCT No.: PCT/EP01/15074

§ 371 (c)(1), (2), (4) Date: Jun. 12, 2003

(87) PCT Pub. No.: WO02/051838

PCT Pub. Date: Jul. 4, 2002

(65) Prior Publication Data

US 2004/0058912 A1    Mar. 25, 2004

(30) Foreign Application Priority Data

Dec. 27, 2000  (WO) ............... PCT/EP00/13289

(51) Int. Cl.
- A61P 3/04 (2006.01)
- A61K 31/55 (2006.01)
- C07D 223/16 (2006.01)

(52) U.S. Cl. ............... 514/213.01; 540/593
(58) Field of Classification Search ....... 514/213.01; 540/593

See application file for complete search history.

(56) References Cited

U.S. PATENT DOCUMENTS 3,236,838 A    2/1966  Archer et al. ............ 260/239.3
3,480,714 A *  11/1969 Harvey ..................... 514/307

FOREIGN PATENT DOCUMENTS

WO    WO 00/21951    4/2000

OTHER PUBLICATIONS

Goff et al., 1995, "Solid-Phase Synthesis of Defined 1,4-Benzodiazepine-2,5-dione Mixtures," J. Org. Chem. 60:5744-5745.

* cited by examiner

*Primary Examiner*—Brenda Coleman

(57) ABSTRACT

The invention relates to novel benzazepines and related heterocyclic derivatives (I) and their use as active ingredients in the preparation of pharmaceutical compositions. The invention also concerns related aspects including processes for the preparation of the compounds, pharmaceutical compositions containing one or more of those compounds and especially their use as orexin receptor antagonists.

5 Claims, No Drawings

BENZAZEPINES AND RELATED HETEROCYCLIC DERIVATIVES WHICH ARE USEFUL AS OREXIN RECEPTOR ANTAGONISTS

CROSS REFERENCE TO RELATED APPLICATIONS

This application is a national stage entry under 35 U.S.C. §371 of PCT/EP01/15074, filed Dec. 19, 2001. This application also claims the priority of PCT/EP00/13289, filed Dec. 27, 2000.

The present invention relates to novel benzazepines and related heterocyclic derivatives of the general formula (I) and their use as pharmaceuticals. The invention also concerns related aspects including processes for the preparation of the compounds, pharmaceutical compositions containing one or more compounds of formula (I), and especially their use as orexin receptor antagonists.

The orexins (hypocretins) comprise two neuropeptides produced in the hypothalamus: the orexin A (OX-A) (a 33 aminoacid peptide) and the orexin B (OX-B) (a 28 aminoacid peptide). Orexins are found-to stimulate food consumption in rats suggesting a physiological role for these peptides as mediators in the central feedback mechanism that regulates feeding behavior (Sakurai T. et al., *Cell* 1998, 92, 573–585). On the other hand, it was also proposed that orexins regulate states of sleep and wakefulness opening potentially novel therapeutic approaches for narcoleptic patients (Chemelli R. M. et al., *Cell* 1999, 98, 437–451). Two orexin receptors have been cloned and characterized in mammals. They belong to the superfamily of G-protein coupled receptor (Sakurai T. et al., *Cell* 1998, 92, 573–585). The orexin-1 receptor ($OX_1$) is selective for OX-A and the orexin-2 receptor ($OX_2$) is capable to bind OX-A as well as OX-B.

Orexin receptors are found in the mammalian host and may be responsible for many biological functions such as pathologies including, but not limited to, depression; anxiety; addictions; obsessive compulsive disorder; affective neurosis; depressive neurosis; anxiety neurosis; dysthymic disorder; behaviour disorder; mood disorder, sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases, inflammatory bowel disease; gastric diskinesia; gastric ulcus; Froehlich's syndrome; adrenohypophysis disease; hypophysis disease; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischaemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; conditions associated with visceral pain such as irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegerative disorders including nosological entities such as disinhibition-dementia-parkinsonism-amyotrophy complex; pallido-ponto-nigral degeneration epilepsy; seizure disorders and other diseases related to orexin.

The present invention provides benzazepines and related heterocyclic derivatives which are non-peptide antagonists of human orexin receptors, in particular $OX_1$ and $OX_2$ receptors. In particular, these compounds are of potential use in the treatment of obesity and/or sleep disorders.

So far not much is known about low molecular weight compounds which have a potential to antagonise either specifically $OX_1$ or $OX_2$ or both receptors at the same time. Recently WO 99/09024, WO 99/58533, WO 00/47577 and WO 00/47580 have been published wherein phenyl urea and phenyl thiourea derivatives are described as being preferably $OX_1$ receptor antagonists. Also quite recently WO 00/47576 described cinnamide derivatives as $OX_1$ receptor antagonists. The novel compounds of the present invention belong to an entirely different class of low molecular weight compounds as compared to all prior art orexin receptor antagonists so far published.

The present invention relates to novel benzazepines and related heterocyclic derivatives of the general formula (I).

General formula (I)

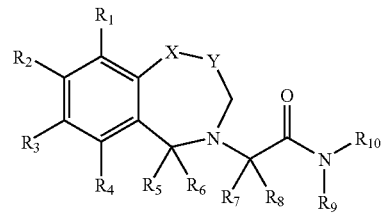

wherein:
$R^1$, $R^2$, $R^3$, $R^4$ independently represent cyano, nitro, halogen, hydrogen, hydroxy, lower alkyl, lower alkenyl, lower alkoxy, lower alkenyloxy, trifluoromethyl, trifluoromethoxy, cycloalkyloxy, aryloxy, aralkyloxy, heterocyclyloxy, heterocyclylalkyloxy, $R^{11}CO—$, $NR^{12}R^{13}CO—$, $R^{12}R^{13}N—$, $R^{11}OOC—$, $R^{11}SO_2NH—$, or $R^{14}—CO—NH—$, or $R^2$ and $R^3$ together as well as $R^1$ and $R^2$ together and $R^3$ and $R^4$ together may form with the phenyl ring a five, six or seven-membered saturated ring containing one or two oxygen atoms;

$R^5$ represents aryl, aralkyl, lower alkyl, lower alkenyl, trifluoromethyl, cycloalkyl, heterocyclyl or heterocyclyl-lower alkyl;

$R^6$ represents hydrogen, aryl, aralkyl, lower alkyl, lower alkenyl, trifluoromethyl, cycloalkyl, heterocyclyl or heterocyclyl-lower alkyl;

$R^7$, $R^8$ independently represent hydrogen, aryl, aralkyl, lower alkyl, lower alkenyl, cycloalkyl, heterocyclyl or heterocyclyl-lower alkyl;

$R^9$, $R^{10}$ independently represent hydrogen, aryl, arylcycloalkyl, aralkyl, lower alkyl, lower alkenyl, lower alkinyl, cycloalkyl, heterocyclyl or heterocyclyl-lower alkyl, in which substituents one, several, or all hydrogen atoms may be replaced by halogen or in which one or two hydrogen atoms may be replaced by hydroxy, nitro, cyano, trifluoromethyl, trifluoromethoxy, —O-lower alkyl, —NH-lower alkyl, —N(lower alkyl)$_2$, —S-lower alkyl, —COO-lower alkyl, —CONH-lower alkyl, —CON(lower alkyl)$_2$, —CO-lower alkyl, —NCO-lower alkyl, —O-lower alkenyl with 3 to 5 carbon atoms, —NH-lower alkenyl with 3 to 5 carbon atoms, —N(lower alkenyl with 3 to 5 carbon atoms)$_2$, —S-lower alkenyl with 3 to 5 carbon atoms, —COO-lower alkenyl with 3 to 5 carbon atoms, —CONH-lower alkenyl with 3 to 5 carbon atoms, —CON(lower alkenyl with 3 to 5 carbon atoms)$_2$, —CO-lower alkenyl with 3 to 5 carbon atoms, —NHCO-lower alkenyl with 3 to 5 carbon atoms, —O-lower alkinyl with 3 to 5 carbon atoms, —NH-lower alkinyl with 3 to 5 carbon atoms, —N(lower alkinyl with 3 to 5 carbon atoms)$_2$, —S-lower alkinyl with 3 to 5 carbon atoms, —COO-lower alkinyl with 3 to 5 carbon atoms, —CONH-lower alkinyl with 3 to 5 carbon atoms, —CON(lower alkinyl with 3 to 5 carbon atoms)$_2$, —CO-lower alkinyl with 3 to 5 carbon atoms, —NHCO-lower alkinyl with 3 to 5 carbon atoms;

$R^{11}$ represents lower alkyl, aryl, aralkyl, heterocyclyl or heterocyclyl-lower alkyl;

$R^{12}$ and $R^{13}$ independently represent hydrogen, lower alkyl, cycloalkyl, aryl, aralkyl, heterocyclyl or heterocyclyl-lower alkyl;

$R^{14}$ represents lower alkyl, aryl, cycloalkyl, heterocyclyl, $R^{12}R^{13}N$—, $R^{11}O$—;

—X—Y— independently represents —CH$_2$—CH$_2$—, —O—CH$_2$—, —S—CH$_2$—, —SO$_2$—CH$_2$— and —NR$^{15}$—CO—;

$R^{15}$ represents hydrogen, lower alkyl or aralkyl;

and optically pure enantiomers, mixtures of enantiomers such as, for example, racemates, optically pure diastereoisomers, mixtures of diastereoisomers, diastereoisomeric racemates, mixtures of diastereoisomeric racemates, or meso forms and pharmaceutically acceptable salts thereof.

In the present description the term "lower alkyl", alone or in combination, signifies a straight-chain or branched-chain alkyl group with 1 to 8 carbon atoms, preferably a straight or branched-chain alkyl group with 1–4 carbon atoms. Examples of straight-chain and branched $C_1$–$C_8$ alkyl groups are methyl, ethyl, n-propyl, isopropyl, n-butyl, n-pentyl, n-hexyl, n-heptyl, n-octyl, isobutyl, tert-butyl, the isomeric pentyls, the isomeric hexyls, the isomeric heptyls and the isomeric octyls, preferably methyl, ethyl, n-propyl, isopropyl, n-butyl, 2-butyl, and tert-butyl.

The term "lower alkenyl", alone or in combination, if not otherwise defined signifies a straight-chain or branched-chain alkenyl group with 2 to 5 carbon atoms, preferably allyl and vinyl.

The term "lower alkinyl", alone or in combination, signifies a straight-chain or branched-chain alkinyl group with 2 to 5 carbon atoms, preferably propargyl and n-butinyl.

The term "lower alkoxy", alone or in combination, signifies a group of the formula lower alkyl-O— in which the term "lower alkyl" has the previously given significance, such as methoxy, ethoxy, n-propoxy, isopropoxy, n-butoxy, isobutoxy, sec-butoxy and tert-butoxy, preferably methoxy and ethoxy.

Lower alkenyloxy groups are preferably vinyloxy and allyloxy.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl groups are cyclopropyl, cyclobutyl, cyclopentyl, cyclohexyl, cycloheptyl and cyclooctyl, preferably cyclopropyl, cyclopentyl, cyclohexyl and particularly cyclohexyl or lower alkyl substituted cycloalkyl which may preferably be substituted with lower alkyl, such as methyl-cyclopropyl, dimethyl-cyclopropyl, methyl-cyclobutyl, methyl-cyclopentyl, methyl-cyclohexyl, dimethyl-cyclohexyl.

The term "aryl", alone or in combination, signifies a phenyl or naphthyl group which optionally carries one or more substituents, preferably one or two substituents, each independently selected from cyano, halogen, hydroxy, lower alkyl, lower alkenyl, lower alkoxy, lower alkenyloxy, nitro, trifluoromethyl, trifluoromethoxy, amino, carboxy and the like, such as phenyl, p-tolyl, 4-methoxyphenyl, 4-tert-butoxyphenyl, 4-fluorophenyl, 2-chlorophenyl, 4-hydroxyphenyl, 1-naphthyl and 2-naphthyl. Preferred are carboxyphenyl, lower alkoxy-phenyl, hydroxyphenyl and particularly phenyl.

The term "aralkyl", alone or in combination, signifies a lower alkyl or cycloalkyl group as previously defined in which one hydrogen atom has been replaced by an aryl group as previously defined. Preferred are benzyl and benzyl substituted in the phenyl ring with hydroxy, lower alkyl, lower alkoxy or halogen preferably chlorine. Particularly preferred is benzyl.

The term "arylcycloalkyl", alone or in combination, signifies an arylcycloalkyl group wherein the cycloalkyl moiety consists of 4 to 7 carbon atoms e.g. indanyl, tetrahydronaphthyl, benzocycloheptyl and benzocyclobutyl. The aromatic moiety may be substituted with one or more substituents, preferably one or two substituents, each independently selected from cyano, halogen, hydroxy, lower alkyl, lower alkenyl, lower alkoxy, lower alkenyloxy, nitro, trifluoromethyl, trifluoromethoxy, amino and carboxy.

For the term "heterocyclyl" and "heterocyclyl-lower alkyl", the heterocyclyl group is preferably a 5- to 10-membered monocyclic or bicyclic ring, which may be saturated, partially unsaturated or aromatic containing for example 1, 2 or 3 heteroatoms selected from oxygen, nitrogen and sulphur which may be the same or different. Example of such heterocyclyl groups are pyrrolidinyl, piperidinyl, piperazinyl, morpholinyl, pyridyl, pyrimidinyl, pyrazinyl, pyridazinyl, quinolyl, isoquinolyl, thienyl, thiazolyl, isothiazolyl, furyl, imidazolyl, pyrazolyl, pyrrolyl, indazolyl, indolyl, isoindolyl, isoxazolyl, oxazolyl, quinoxalinyl, phthalazinyl, cinnolinyl, dihydropyrrolyl, isobenzofuranyl, tetrahydrofuranyl, dihydropyranyl. The heterocyclyl group may have up to 5, preferably 1, 2 or 3 optional substituents. Examples of suitable substituents include halogen, lower alkyl, amino, nitro, cyano, hydroxy, lower alkoxy, carboxy and lower alkyloxy-carbonyls.

The term "halogen" signifies fluorine, chlorine, bromine or iodine and preferably fluorine and chlorine.

The term "carboxy", alone or in combination, signifies a —COOH group.

A group of preferred compounds according to the present invention are compounds of formula (II)

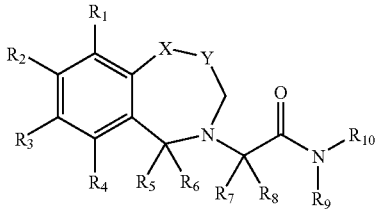

Formula (II)

wherein:
R¹, R², R³, R⁴ independently represent cyano, nitro, halogen, hydrogen, hydroxy, lower alkyl, lower alkenyl, lower alkoxy, lower alkenyloxy, trifluoromethyl, trifluoromethoxy, cycloalkyloxy, aryloxy, aralkyloxy, heterocyclyloxy, heterocyclylalkyloxy, R¹¹CO—, NR¹²R¹³CO—, R¹²R¹³N—, R¹¹OOC—, R¹¹SO₂NH—, or R¹⁴—CO—NH—, or R² and R³ together as well as R¹ and R² together and R³ and R⁴ together may form with the phenyl ring a five, six or seven-membered saturated ring containing one or two oxygen atoms;

R⁵ represents aryl, aralkyl, lower alkyl, lower alkenyl, trifluoromethyl, cycloalkyl, heterocyclyl or heterocyclyl-lower alkyl;

R⁶ represents hydrogen, aryl, aralkyl, lower alkyl, lower alkenyl, trifluoromethyl, cycloalkyl, heterocyclyl or heterocyclyl-lower alkyl;

R⁷, R⁸, R⁹, R¹⁰ independently represent hydrogen, aryl, aralkyl, lower alkyl, lower alkenyl, cycloalkyl, heterocyclyl or heterocyclyl-lower alkyl;

R¹¹ represents lower alkyl, aryl, aralkyl, heterocyclyl or heterocyclyl-lower alkyl;

R¹² and R¹³ independently represent hydrogen, lower alkyl, cycloalkyl, aryl, aralkyl, heterocyclyl or heterocyclyl-lower alkyl;

R¹⁴ represents lower alkyl, aryl, cycloalkyl, heterocyclyl, R¹²R¹³N—, R¹¹O—;

—X—Y— independently represents —CH₂—CH₂—, —O—CH₂—, —S—CH₂—, —SO₂—CH₂— and —NR¹⁵—CO—;

R¹⁵ represents hydrogen, lower alkyl or aralkyl;

and optically pure enantiomers, mixtures of enantiomers such as, for example, racemates, optically pure diastereoisomers, mixtures of diastereoisomers, diastereoisomeric racemates, mixtures of diastereoisomeric racemates, or meso forms and pharmaceutically acceptable salts thereof.

Another group of preferred compounds according to the present invention are compounds of formula (III)

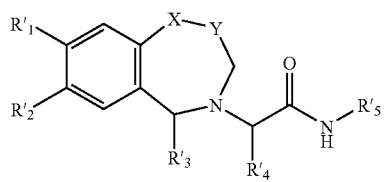

Formula (III)

wherein:
R'¹ and R'² independently represent hydrogen, hydroxy, lower alkoxy, lower alkenyloxy or halogen or may form with the phenyl ring a five, six or seven membered-ring containing one or two oxygen atoms;

R'³ represents aryl, aralkyl, lower alkyl, lower alkenyl, cycloalkyl, heterocyclyl or heterocyclyl-lower alkyl;

R'⁴, R'⁵ independently represent hydrogen, aryl, aralkyl, lower alkyl, lower alkenyl, cycloalkyl, heterocyclyl or heterocyclyl-lower alkyl;

—X—Y— independently represents —CH₂—CH₂—, —O—CH₂—, —S—CH₂—, —SO₂—CH₂— and —NR'⁶—CO—;

R'⁶ represents hydrogen, lower alkyl or aralkyl;

and optically pure enantiomers, mixtures of enantiomers such as, for example, racemates, optically pure diastereoisomers, mixtures of diastereoisomers, diastereoisomeric racemates, mixture of diastereoisomeric racemates, or meso forms and pharmaceutically acceptable salts thereof.

Examples of preferred compounds are:

2-[1-(3,4-Dimethoxy-benzyl)-7,8-dimethoxy-1,3,4,5-tetrahydro-benzo[c]azepin-2-yl]-N-naphthalen-1-ylmethyl-acetamide N-Benzo[1,3]dioxol-5-ylmethyl-2-[1-(3,4-dimethoxy-benzyl)-7,8-dimethoxy-1,3,4,5-tetrahydro-benzo[c]azepin-2-yl]-acetamide 2-[1-(3,4-Dimethoxy-benzyl)-7,8-dimethoxy-1,3,4,5-tetrahydro-benzo[c]azepin-2-yl]-N-indan-2-yl-acetamide 2-[5-(3,4-Dimethoxy-benzyl)-7,8-dimethoxy-2,3-dihydro-5H-benzo[f][1,4]oxazepin-4-yl]-N-indan-2-yl-acetamide 2-[5-(3,4-Dimethoxy-benzyl)-7,8-dimethoxy-2,3-dihydro-5H-benzo[f][1,4]oxazepin-4-yl]-N-indan-1-yl-acetamide 2-[1-(3,4-Dimethoxy-benzyl)-7,8-dimethoxy-1,3,4,5-tetrahydro-benzo[c]azepin-2-yl]-N-indan-1-yl-acetamide 2-[9-(3,4-Dimethoxy-benzyl)-2,3-dimethoxy-5,5-dioxo-5,6,7,9-tetrahydro-5λ-thia-8-aza-benzocyclohepten-8-yl]-N-indan-2-yl-acetamide 2-[9-(3,4-Dimethoxy-benzyl)-2,3-dimethoxy-5,5-dioxo-5,6,7,9-tetrahydro-5λ-thia-8-aza-benzocyclohepten-8-yl]-N-indan-1-yl-acetamide 2-[1-(3,4-Dimethoxy-benzyl)-7,8-dimethoxy-1,3,4,5-tetrahydro-benzo[c]azepin-2-yl]-N-indan-1-yl-acetamide 2-[1-(3,4-Dimethoxy-benzyl)-7,8-dimethoxy-1,3,4,5-tetrahydro-benzo[c]azepin-2-yl]-N-indan-2-yl-2-phenyl-acetamide 2-[9-(3,4-Dimethoxy-benzyl)-2,3-dimethoxy-6,7-dihydro-9H-5-thia-8-aza-benzocyclohepten-8-yl]-N-naphthalen-1-ylmethyl-acetamide 2-[9-(3,4-Dimethoxy-benzyl)-2,3-dimethoxy-6,7-dihydro-9H-5-thia-8-aza-benzocyclohepten-8-yl]-N-(2-ethoxy-benzyl)-acetamide 2-[9-(3,4-Dimethoxy-benzyl)-2,3-dimethoxy-6,7-dihydro-9H-5-thia-8-aza-benzocyclohepten-8-yl]-N-indan-1-yl-acetamide 2-[5-(3,4-Dimethoxy-benzyl)-7,8-dimethoxy-2,3-dihydro-5H-benzo[f][1,4]oxazepin-4-yl]-N-(1,2,3,4-tetrahydro-naphthalen-1-yl)-acetamide N-Benzyl-2-[9-(3,4-dimethoxy-benzyl)-2,3-dimethoxy-6,7-dihydro-9H-5-thia-8-aza-benzocyclohepten-8-yl]-acetamide 2-[5-(3,4-Dimethoxy-benzyl)-7,8-dimethoxy-2,3-dihydro-5H-benzo[f][1,4]oxazepin-4-yl]-N-indan-1-yl-acetamide N-Butyl-2-[1-(3,4-dimethoxy-benzyl)-7,8-dimethoxy-1,3,4,5-tetrahydro-benzo[c]azepin-2-yl]-2-phenyl-acetamide 2-[1-(3,4-Dimethoxy-benzyl)-7,8-dimethoxy-1,3,4,5-tetrahydro-benzo[c]azepin-2-yl]-N-indan-1-yl-2-phenyl-acetamide N-Benzo[1,3]dioxol-5-ylmethyl-2-[1-(3,4-dimethoxy-benzyl)-7,8-dimethoxy-1,3,4,5-tetrahydro-benzo[c]azepin-2-yl]-2-phenyl-acetamide N-Cyclopentyl-2-[1-(3,4-dimethoxy-benzyl)-7,8-dimethoxy-1,3,4,5-tetrahydro-benzo[c]azepin-2-yl]-2-phenyl-acetamide 2-[1-(3,4-Dimethoxy-benzyl)-7,8-dimethoxy-1,3,4,5-tetrahydro-benzo[c]azepin-2-yl]-N-furan-2-ylmethyl-2-phenyl-acetamide {2-[1-(3,4-Dimethoxy-benzyl)-7,8-dimethoxy-1,3,4,5-tetrahydro-benzo[c]azepin-2-yl]-2-phenyl-acetylamino}-acetic acid ethyl ester 2-[1-(3,4-Dimethoxy-benzyl)-7,8-dimethoxy-1,3,4,5-tetrahydro-benzo[c]azepin-2-yl]-2-phenyl-N-pyridin-4-ylmethyl-acetamide 2-[1-(3,4-Dimethoxy-benzyl)-7,8-dimethoxy-1,3,4,5-tetrahydro-benzo[c]azepin-2-yl]-2-phenyl-N-pyridin-3-ylmethyl-acetamide N-Cyclopropyl-2-[1-(3,4-dimethoxy-benzyl)-7,8-dimethoxy-1,3,4,5-tetrahydro-benzo[c]azepin-2-yl]-2-phenyl-acetamide 2-[1-(3,4-Dimethoxy-benzyl)-7,8-dimethoxy-1,3,4,5-tetrahydro-benzo[c]azepin-2-yl]-N-(2-oxo-tetrahydro-furan-3-yl)-2-phenyl-acetamide 2-[1-(3,4-Dimethoxy-benzyl)-7,8-dimethoxy-1,3,4,5-tetrahydro-benzo[c]azepin-2-yl]-N-(4-methoxy-indan-1-yl)-acetamide 2-[1-(3,4-Dimethoxy-benzyl)-7,8-dimethoxy-1,3,4,5-tetrahydro-benzo[c]azepin-2-yl]-N-(3-phenyl-indan-1-yl)-acetamide 2-[1-(3,4-Dimethoxy-benzyl)-7,8-dimethoxy-1,3,4,5-tetrahydro-benzo[c]azepin-2-yl]-N-(4-methyl-indan-1-yl)-acetamide 2-{2-[1-(3,4-Dimethoxy-benzyl)-7,8-dimethoxy-1,3,4,5-tetrahydro-benzo[c]azepin-2-yl]-2-phenyl-acetylamino}-3-hydroxy-propionic acid methyl ester 2-[1-(3,4-Dimethoxy-benzyl)-7,8-dimethoxy-1,3,4,5-tetrahydro-benzo[c]azepin-2-yl]-N-ethylcarbamoylmethyl-2-phenyl-acetamide 2-[1-(3,4-Dimethoxy-benzyl)-7,8-dimethoxy-1,3,4,5-tetrahydro-benzo[c]azepin-2-yl]-N-[(ethyl-methyl-carbamoyl)-methyl]-2-phenyl-acetamide 2-[1-(3,4-Dimethoxy-benzyl)-8-hydroxy-7-methoxy-1,3,4,5-tetrahydro-benzo[c]azepin-2-yl]-N-indan-1-yl-acetamide 2-[8-Benzyloxy-1-(3,4-dimethoxy-benzyl)-7-methoxy-1,3,4,5-tetrahydro-benzo[c]azepin-2-yl]-N-indan-1-yl-acetamide 3-{2-[1-(3,4-Dimethoxy-benzyl)-7,8-dimethoxy-1,3,4,5-tetrahydro-benzo[c]azepin-2-yl]-2-phenyl-acetylamino}-propionic acid methyl ester N-Benzo[1,3]dioxol-5-ylmethyl-2-[1-(3,4-dimethoxy-benzyl)-8-hydroxy-7-methoxy-1,3,4,5-tetrahydro-benzo[c]azepin-2-yl]-2-phenyl-acetamide N-(1H-Benzoimidazol-2-ylmethyl)-2-[1-(3,4-dimethoxy-benzyl)-7,8-dimethoxy-1,3,4,5-tetrahydro-benzo[c]azepin-2-yl]-2-phenyl-acetamide 3-{2-[1-(3,4-Dimethoxy-benzyl)-7,8-dimethoxy-1,3,4,5-tetrahydro-benzo[c]azepin-2-yl]-2-phenyl-acetylamino}-N,N-dimethyl-propionamide 3-{2-[1-(3,4-Dimethoxy-benzyl)-7,8-dimethoxy-1,3,4,5-tetrahydro-benzo[c]azepin-2-yl]-2-phenyl-acetylamino}-N-ethyl-N-methyl-propionamide 2-[1-(3,4-Dimethoxy-benzyl)-7,8-dimethoxy-1,3,4,5-tetrahydro-benzo[c]azepin-2-yl]-N-(1-methyl-1H-indol-3-ylmethyl)-2-phenyl-acetamide 2-[1-(3,4-Dimethoxy-benzyl)-7,8-dimethoxy-1,3,4,5-tetrahydro-benzo[c]azepin-2-yl]-N-isoxazol-5-ylmethyl-2-phenyl-acetamide 2-[1-(3,4-Dimethoxy-benzyl)-7,8-dimethoxy-1,3,4,5-tetrahydro-benzo[c]azepin-2-yl]-N-(1H-indol-3-ylmethyl)-2-phenyl-acetamide 2-[1-(3,4-Dimethoxy-benzyl)-7,8-dimethoxy-1,3,4,5-tetrahydro-benzo[c]azepin-2-yl]-N-(1-methyl-1H-benzoimidazol-2-ylmethyl)-2-phenyl-acetamide 2-[1-(3,4-Dimethoxy-benzyl)-7,8-dimethoxy-1,3,4,5-tetrahydro-benzo[c]azepin-2-yl]-N-isoquinolin-1-ylmethyl-2-phenyl-acetamide 2-[1-(3,4-Dimethoxy-benzyl)-7,8-dimethoxy-1,3,4,5-tetrahydro-benzo[c]azepin-2-yl]-2-phenyl-N-(4-[1,2,3]thiadiazol-4-yl-benzyl)-acetamide 2-[1-(3,4-Dimethoxy-benzyl)-7,8-dimethoxy-1,3,4,5-tetrahydro-benzo[c]azepin-2-yl]-N-(1-methyl-1H-indazol-3-ylmethyl)-2-phenyl-acetamide N-Cyanomethyl-2-[1-(3,4-dimethoxy-benzyl)-7,8-dimethoxy-1,3,4,5-tetrahydro-benzo[c]azepin-2-yl]-2-phenyl-acetamide N-(2-Acetylamino-ethyl)-2-[1-(3,4-dimethoxy-benzyl)-7,8-dimethoxy-1,3,4,5-tetrahydro-benzo[c]azepin-2-yl]-2-phenyl-acetamide 2-[1-(3,4-Dimethoxy-benzyl)-7,8-dimethoxy-1,3,4,5-tetrahydro-benzo[c]azepin-2-yl]-2-phenyl-N-(2,2,2-trifluoro-ethyl)-acetamide 2-[1-(3,4-Dimethoxy-benzyl)-7,8-dimethoxy-1,3,4,5-tetrahydro-benzo[c]azepin-2-yl]-N-(2-methylsulfanyl-ethyl)-2-phenyl-acetamide 2-[1-(3,4-Dimethoxy-benzyl)-7,8-dimethoxy-1,3,4,5-tetrahydro-benzo[c]azepin-2-yl]-2-phenyl-N-quinolin-2-ylmethyl-acetamide N-(2–Cyano-ethyl)-2-[1-(3,4-dimethoxy-benzyl)-7,8-dimethoxy-1,3,4,5-tetrahydro-benzo[c]azepin-2-yl]-2-phenyl-acetamide 2-[1-(3,4-Dimethoxy-benzyl)-7,8-dimethoxy-1,3,4,5-tetrahydro-benzo[c]azepin-2-yl]-N-(3-methoxy-propyl)-2-phenyl-acetamide 2-[1-(3,4-Dimethoxy-benzyl)-7,8-dimethoxy-1,3,4,5-tetrahydro-benzo[c]azepin-2-yl]-N-(3-ethoxy-propyl)-2-phenyl-acetamide 2-[1-(3,4-Dimethoxy-benzyl)-7,8-dimethoxy-1,3,4,5-tetrahydro-benzo[c]azepin-2-yl]-2-phenyl-acetamide 2-[1-(3,4-Dimethoxy-benzyl)-7,8-dimethoxy-1,3,4,5-tetrahydro-benzo[c]azepin-2-yl]-2-phenyl-N-pyrazin-2-ylmethyl-acetamide 2-[1-(3,4-Dimethoxy-benzyl)-7,8-dimethoxy-1,3,4,5-tetrahydro-benzo[c]azepin-2-yl]-2-phenyl-N-prop-2-ynyl-acetamide N-tert-Butyl-2-[1-(3,4-dimethoxy-benzyl)-7,8-dimethoxy-1,3,4,5-tetrahydro-benzo[c]azepin-2-yl]-2-phenyl-acetamide 2-[1-(3,4-Dimethoxy-benzyl)-7,8-dimethoxy-1,3,4,5-tetrahydro-benzo[c]azepin-2-yl]-N-(3-methyl-butyl)-2-phenyl-acetamide 2-[1-(3,4-Dimethoxy-benzyl)-7,8-dimethoxy-1,3,4,5-tetrahydro-benzo[c]azepin-2-yl]-N-(3,3-dimethyl-butyl)-2-phenyl-acetamide 2-[1-(3,4-Dimethoxy-benzyl)-7,8-dimethoxy-1,3,4,5-tetrahydro-benzo[c]azepin-2-yl]-N-(1-ethyl-propyl)-2-phenyl-acetamide 2-[1-(3,4-Dimethoxy-benzyl)-7,8-dimethoxy-1,3,4,5-tetrahydro-benzo[c]azepin-2-yl]-N-(2-ethylsulfanyl-ethyl)-2-phenyl-acetamide 2-[1-(3,4-Dimethoxy-benzyl)-7,8-dimethoxy-1,3,4,5-tetrahydro-benzo[c]azepin-2-yl]-N-(2-hydroxy-ethyl)-2-phenyl-acetamide
2-[1-(3,4-Dimethoxy-benzyl)-7,8-dimethoxy-1,3,4,5-tetrahydro-benzo[c]azepin-2-yl]-N-(3-hydroxy-propyl)-2-phenyl-acetamide
[1-(3,4-Dimethoxy-benzyl)-7,8-dimethoxy-1,3,4,5-tetrahydro-benzo[c]azepin-2-yl]-phenyl-acetic acid N',N'-dimethyl-hydrazide
2-[8-Allyloxy-1-(3,4-dimethoxy-benzyl)-7-methoxy-1,3,4,5-tetrahydro-benzo[c]azepin-2-yl]-N-indan-1-yl-acetamide
2-[1-(3,4-Dimethoxy-benzyl)-7-methoxy-8-propoxy-1,3,4,5-tetrahydro-benzo[c]azepin-2-yl]-N-indan-1-yl-acetamide
2-[1-(3,4-Dimethoxy-benzyl)-8-isopropoxy-7-methoxy-1,3,4,5-tetrahydro-benzo[c]azepin-2-yl]-N-indan-1-yl-acetamide
2-[8-(2,2-Difluoro-ethoxy)-1-(3,4-dimethoxy-benzyl)-7-methoxy-1,3,4,5-tetrahydro-benzo[c]azepin-2-yl]-N-indan-1-yl-acetamide
N-Benzo[1,3]dioxol-5-ylmethyl-2-[8-(2,2-difluoro-ethoxy)-1-(3,4-dimethoxy-benzyl)-7-methoxy-1,3,4,5-tetrahydro-benzo[c]azepin-2-yl]-2-phenyl-acetamide
N-Benzo[1,3]dioxol-5-ylmethyl-2-[1-(3,4-dimethoxy-benzyl)-8-isopropoxy-7-methoxy-1,3,4,5-tetrahydro-benzo[c]azepin-2-yl]-2-phenyl-acetamide
2-[5-(3,4-Dichloro-benzyl)-7,8-dimethoxy-2-oxo-1,2,3,5-tetrahydro-benzo[e][1,4]diazepin-4-yl]-N-indan-1-yl-acetamide
2-[1-(S)-(3,4-Dimethoxy-benzyl)-7,8-dimethoxy-1,3,4,5-tetrahydro-benzo[c]azepin-2-yl]-N-indan-1-yl-acetamide
2-[1-(S)-(3,4-Dimethoxy-benzyl)-7,8-dimethoxy-1,3,4,5-tetrahydro-benzo[c]azepin-2-yl]-N-indan-2-yl-acetamide
Examples of particularly preferred compounds are:
2-[1-(3,4-Dimethoxy-benzyl)-7,8-dimethoxy-1,3,4,5-tetrahydro-benzo[c]azepin-2-yl]-N-indan-2-yl-acetamide
2-[5-(3,4-Dimethoxy-benzyl)-7,8-dimethoxy-2,3-dihydro-5H-benzo[f][1,4]oxazepin-4-yl]-N-indan-1-yl-acetamide
2-[1-(3,4-Dimethoxy-benzyl)-7,8-dimethoxy-1,3,4,5-tetrahydro-benzo[c]azepin-2-yl]-N-indan-1-yl-acetamide
2-[1-(3,4-Dimethoxy-benzyl)-7,8-dimethoxy-1,3,4,5-tetrahydro-benzo[c]azepin-2-yl]-N-indan-1-yl-acetamide
2-[1-(3,4-Dimethoxy-benzyl)-7,8-dimethoxy-1,3,4,5-tetrahydro-benzo[c]azepin-2-yl]-N-indan-2-yl-2-phenyl-acetamide
N-Butyl-2-[1-(3,4-dimethoxy-benzyl)-7,8-dimethoxy-1,3,4,5-tetrahydro-benzo[c]azepin-2-yl]-2-phenyl-acetamide
2-[1-(3,4-Dimethoxy-benzyl)-7,8-dimethoxy-1,3,4,5-tetrahydro-benzo[c]azepin-2-yl]-N-indan-1-yl-2-phenyl-acetamide
N-Benzo[1,3]dioxol-5-ylmethyl-2-[1-(3,4-dimethoxy-benzyl)-7,8-dimethoxy-1,3,4,5-tetrahydro-benzo[c]azepin-2-yl]-2-phenyl-acetamide
N-Cyclopentyl-2-[1-(3,4-dimethoxy-benzyl)-7,8-dimethoxy-1,3,4,5-tetrahydro-benzo[c]azepin-2-yl]-2-phenyl-acetamide
2-[1-(3,4-Dimethoxy-benzyl)-7,8-dimethoxy-1,3,4,5-tetrahydro-benzo[c]azepin-2-yl]-N-furan-2-ylmethyl-2-phenyl-acetamide
{2-[1-(3,4-Dimethoxy-benzyl)-7,8-dimethoxy-1,3,4,5-tetrahydro-benzo[c]azepin-2-yl]-2-phenyl-acetylamino}-acetic acid ethyl ester
2-[1-(3,4-Dimethoxy-benzyl)-7,8-dimethoxy-1,3,4,5-tetrahydro-benzo[c]azepin-2-yl]-2-phenyl-N-pyridin-3-ylmethyl-acetamide
3-{2-[1-(3,4-Dimethoxy-benzyl)-7,8-dimethoxy-1,3,4,5-tetrahydro-benzo[c]azepin-2-yl]-2-phenyl-acetylamino}-propionic acid methyl ester
N-(1H-Benzoimidazol-2-ylmethyl)-2-[1-(3,4-dimethoxy-benzyl)-7,8-dimethoxy-1,3,4,5-tetrahydro-benzo[c]azepin-2-yl]-2-phenyl-acetamide
2-[1-(3,4-Dimethoxy-benzyl)-7,8-dimethoxy-1,3,4,5-tetrahydro-benzo[c]azepin-2-yl]-N-(1-methyl-1H-indol-3-ylmethyl)-2-phenyl-acetamide
2-[1-(3,4-Dimethoxy-benzyl)-7,8-dimethoxy-1,3,4,5-tetrahydro-benzo[c]azepin-2-yl]-N-isoxazol-5-ylmethyl-2-phenyl-acetamide
2-[1-(3,4-Dimethoxy-benzyl)-7,8-dimethoxy-1,3,4,5-tetrahydro-benzo[c]azepin-2-yl]-N-(1H-indol-3-ylmethyl)-2-phenyl-acetamide
2-[1-(3,4-Dimethoxy-benzyl)-7,8-dimethoxy-1,3,4,5-tetrahydro-benzo[c]azepin-2-yl]-N-isoquinolin-1-ylmethyl-2-phenyl-acetamide
2-[1-(3,4-Dimethoxy-benzyl)-7,8-dimethoxy-1,3,4,5-tetrahydro-benzo[c]azepin-2-yl]-2-phenyl-N-(4-[1,2,3]thiadiazol-4-yl-benzyl)-acetamide
2-[1-(3,4-Dimethoxy-benzyl)-7,8-dimethoxy-1,3,4,5-tetrahydro-benzo[c]azepin-2-yl]-N-(1-methyl-1H-indazol-3-ylmethyl)-2-phenyl-acetamide
N-Cyanomethyl-2-[1-(3,4-dimethoxy-benzyl)-7,8-dimethoxy-1,3,4,5-tetrahydro-benzo[c]azepin-2-yl]-2-phenyl-acetamide
2-[1-(3,4-Dimethoxy-benzyl)-7,8-dimethoxy-1,3,4,5-tetrahydro-benzo[c]azepin-2-yl]-2-phenyl-N-(2,2,2-trifluoro-ethyl)-acetamide
2-[1-(3,4-Dimethoxy-benzyl)-7,8-dimethoxy-1,3,4,5-tetrahydro-benzo[c]azepin-2-yl]-N-(2-methylsulfanyl-ethyl)-2-phenyl-acetamide
2-[1-(3,4-Dimethoxy-benzyl)-7,8-dimethoxy-1,3,4,5-tetrahydro-benzo[c]azepin-2-yl]-2-phenyl-N-quinolin-2-ylmethyl-acetamide
N-(2-Cyano-ethyl)-2-[1-(3,4-dimethoxy-benzyl)-7,8-dimethoxy-1,3,4,5-tetrahydro-benzo[c]azepin-2-yl]-2-phenyl-acetamide
2-[1-(3,4-Dimethoxy-benzyl)-7,8-dimethoxy-1,3,4,5-tetrahydro-benzo[c]azepin-2-yl]-N-(3-methoxy-propyl)-2-phenyl-acetamide
2-[1-(3,4-Dimethoxy-benzyl)-7,8-dimethoxy-1,3,4,5-tetrahydro-benzo[c]azepin-2-yl]-N-(3-ethoxy-propyl)-2-phenyl-acetamide
2-[1-(3,4-Dimethoxy-benzyl)-7,8-dimethoxy-1,3,4,5-tetrahydro-benzo[c]azepin-2-yl]-2-phenyl-N-pyrazin-2-ylmethyl-acetamide
2-[1-(3,4-Dimethoxy-benzyl)-7,8-dimethoxy-1,3,4,5-tetrahydro-benzo[c]azepin-2-yl]-2-phenyl-N-prop-2-ynyl-acetamide
2-[1-(3,4-Dimethoxy-benzyl)-7,8-dimethoxy-1,3,4,5-tetrahydro-benzo[c]azepin-2-yl]-N-(3-methyl-butyl)-2-phenyl-acetamide
2-[1-(3,4-Dimethoxy-benzyl)-7,8-dimethoxy-1,3,4,5-tetrahydro-benzo[c]azepin-2-yl]-N-(3,3-dimethyl-butyl)-2-phenyl-acetamide
2-[1-(3,4-Dimethoxy-benzyl)-7,8-dimethoxy-1,3,4,5-tetrahydro-benzo[c]azepin-2-yl]-N-(1-ethyl-propyl)-2-phenyl-acetamide
2-[1-(3,4-Dimethoxy-benzyl)-7,8-dimethoxy-1,3,4,5-tetrahydro-benzo[c]azepin-2-yl]-N-(2-ethylsulfanyl-ethyl)-2-phenyl-acetamide 2-[1-(3,4-Dimethoxy-benzyl)-7,8-dimethoxy-1,3,4,5-tetrahydro-benzo[c]azepin-2-yl]-N-(2-hydroxy-ethyl)-2-phenyl-acetamide 2-[8-Allyloxy-1-(3,4-dimethoxy-benzyl)-7-methoxy-1,3,4,5-tetrahydro-benzo[c]azepin-2-yl]-N-indan-1-yl-acetamide 2-[1-(3,4-Dimethoxy-benzyl)-7-methoxy-8-propoxy-1,3,4,5-tetrahydro-benzo[c]azepin-2-yl]-N-indan-1-yl-acetamide 2-[1-(3,4-Dimethoxy-benzyl)-8-isopropoxy-7-methoxy-1,3,4,5-tetrahydro-benzo[c]azepin-2-yl]-N-indan-1-yl-acetamide 2-[8-(2,2-Difluoro-ethoxy)-1-(3,4-dimethoxy-benzyl)-7-methoxy-1,3,4,5-tetrahydro-benzo[c]azepin-2-yl]-N-indan-1-yl-acetamide N-Benzo[1,3]dioxol-5-ylmethyl-2-[8-(2,2-difluoro-ethoxy)-1-(3,4-dimethoxy-benzyl)-7-methoxy-1,3,4,5-tetrahydro-benzo[c]azepin-2-yl]-2-phenyl-acetamide N-Benzo[1,3]dioxol-5-ylmethyl-2-[1-(3,4-dimethoxy-benzyl)-8-isopropoxy-7-methoxy-1,3,4,5-tetrahydro-benzo[c]azepin-2-yl]-2-phenyl-acetamide 2-[1-(S)-(3,4-Dimethoxy-benzyl)-7,8-dimethoxy-1,3,4,5-tetrahydro-benzo[c]azepin-2-yl]-N-indan-1-yl-acetamide 2-[1-(S)-(3,4-Dimethoxy-benzyl)-7,8-dimethoxy-1,3,4,5-tetrahydro-benzo[c]azepin-2-yl]-N-indan-2-yl-acetamide Examples of physiologically usable or pharmaceutically acceptable salts of the compounds of general formula (I) are salts with physiologically compatible mineral acids such as hydrochloric acid, sulfuric or phosphoric acid, or with organic acids such as methanesulphonic acid, acetic acid, trifluoroacetic acid, citric acid, fumaric acid, maleic acid, tartaric acid, succinic acid or salicylic acid. Compounds of formula (I) with acidic groups can also form salts with physiologically compatible bases. Examples of such salts are alkali metal, earth alkali metal, ammonium and alkylammonium salts such as Na, K, Ca or tetraalkylammonium salts. The compounds of general formula (I) can also be present in the form of a zwitterion.

Preferred compounds as described above have $IC_{50}$ values below 1000 nM; particularly preferred compounds have $IC_{50}$ values below 100 nM which have been determinated with the FLIPR (Fluorometric Imaging Plates Reader) method described in the beginning of the experimental section.

The compounds of the general formula (I) and their pharmaceutically usable salts can be used for the treatment of diseases or disorders where an antagonist of a human orexin receptor is required such as obesity, diabetes, cardiovascular disorders, cancer, prolactinoma, pain, narcolepsy, insomnia, sleep apnea, parasomnia, depression, anxiety, addictions, schizophrenia, neurodegenerative disorders and dementia.

The compounds of general formula (I) and their pharmaceutically usable salts are particularly useful for the treatment of obesity and sleep disorders.

The compounds of general formula (I) and their pharmaceutically usable salts can be used as medicament (e.g. in the form of pharmaceutical preparations). The pharmaceutical preparations can be administered in enteral or oral form (e.g. in the form of tablets, coated tablets, dragées, hard and soft gelatine capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions).

The compounds of general formula (I) and their pharmaceutically usable salts can be processed with pharmaceutically inert, inorganic or organic excipients for the production of tablets, coated tablets, dragées, and hard gelatine capsules. Lactose, corn starch or derivatives thereof, talc, stearic acid or its salts etc. can be used, for example, as such adjuvants for tablets, dragées, and hard gelatine capsules.

Suitable adjuvants for soft gelatine capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances. The invention also relates to processes for the preparation of compounds of general formula (I).

The compounds of general formula (I) of the present invention are prepared according to the general sequence of reactions outlined in the schemes below, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ are as defined in general formula (I) above. As the case may be any compound obtained with one or more optically active carbon atom may be resolved into pure enantiomers or diastereomers, mixtures of enantiomers or diastereomers, diastereomeric racemates and the meso-forms in a manner known per se.

The compounds obtained may also be converted into a pharmaceutically acceptable salt thereof in a manner known per se.

The compounds of the general formula (I) may be prepared by standard procedures (Procedure A wherein $R^7$ and $R^8$ are hydrogen atoms and Procedure B wherein $R^7$ and/or $R^8$ are other than hydrogen) shown in Scheme 1 using synthesized benzazepine and related heterocyclic derivatives.

Scheme 1
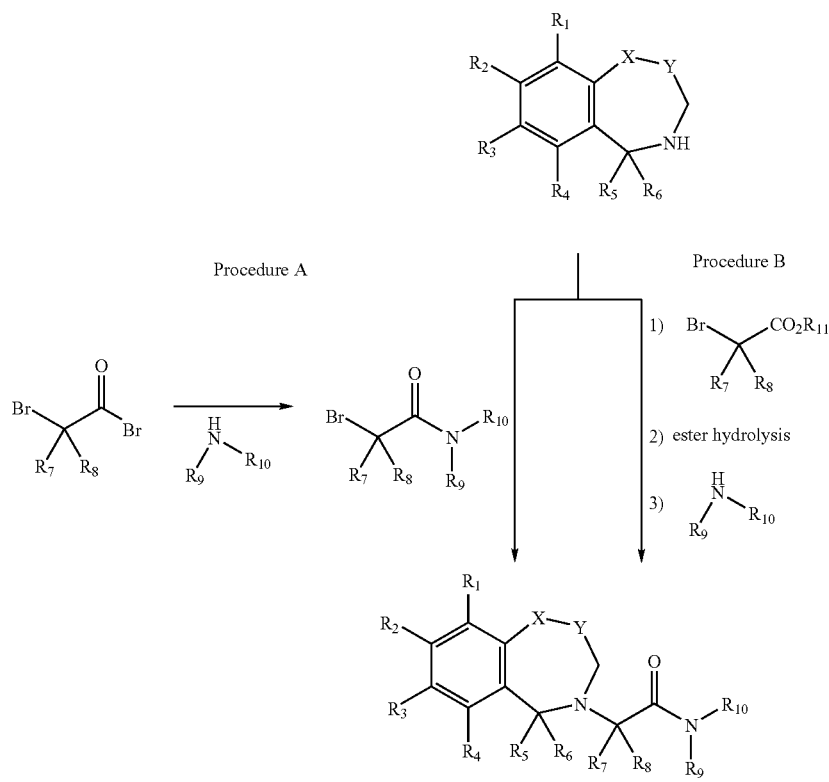
Benzazepine derivatives wherein X and Y are CH$_2$ and R$^6$ is hydrogen might be prepared from the corresponding phenylpropylamine by coupling with the desired carboxylic acid or acyl chloride followed by treatment with POCl$_3$ and finally NaBH$_4$ (Bischler-Napieralski reaction) as shown in Scheme 2a (S. Kano et al., *Chem. Pharm. Bull.* 1977, 25, 10, 2510–2515).
Scheme 2a
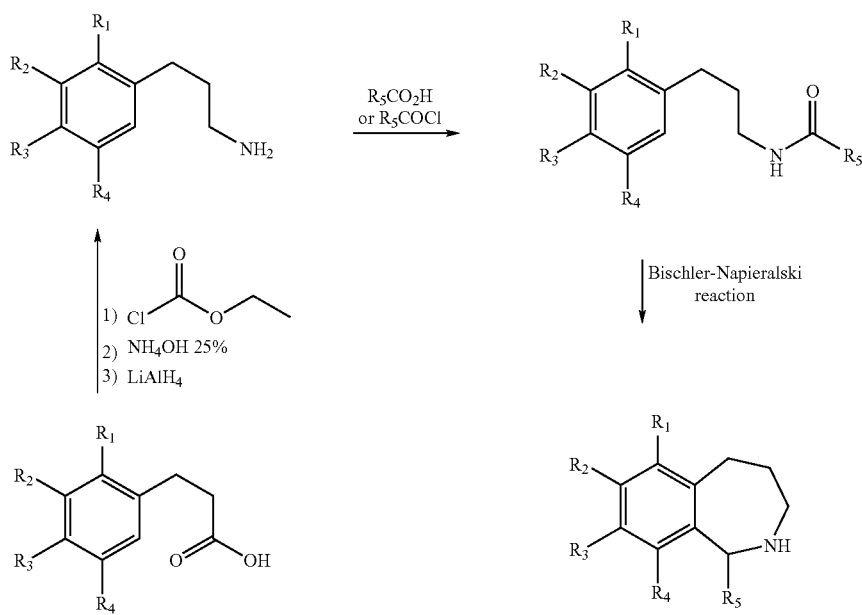

Benzazepines with variable substituents on position 8 might be prepared by hydrogenolysis of the corresponding 8-benzyloxy-1,3,4,5-tetrahydro-benzazepines followed by O-alkylation with the appropriate electrophile (Scheme 2b, —OR'$_{11}$ being included in the definition of R$_3$). The benzylethers can be obtained with the previous procedure (Scheme 2a) applied to 3-(4-benzyloxy-phenyl)-propionic acid derivatives.

Scheme 2b

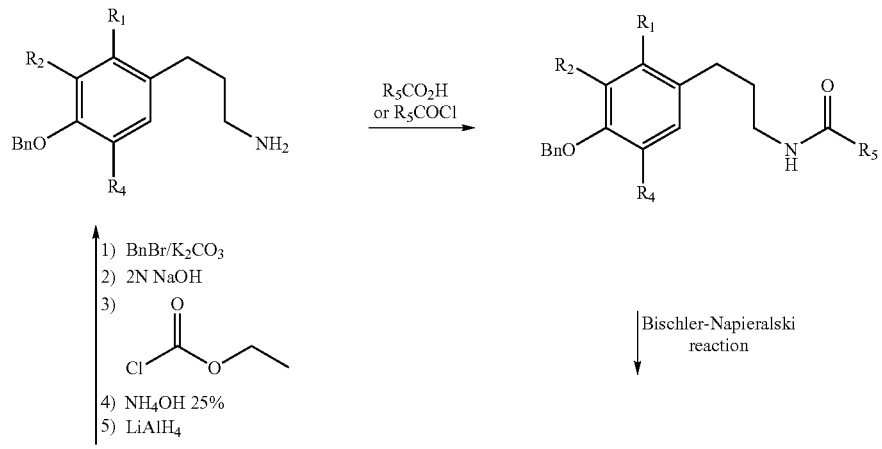

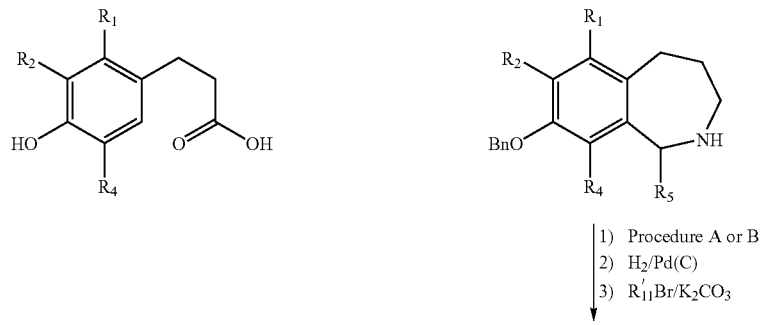

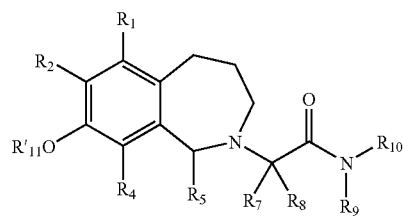

Benzothiazepine and benzoxazepine derivatives wherein X is O or S, Y is $CH_2$ and $R^6$ is hydrogen might be prepared from the corresponding arylamine by coupling with the desired carboxylic acid or acyl chloride followed by treatment with $POCl_3$ and finally $NaBH_4$ (Bischler-Napieralski reaction) as shown in Scheme 3.

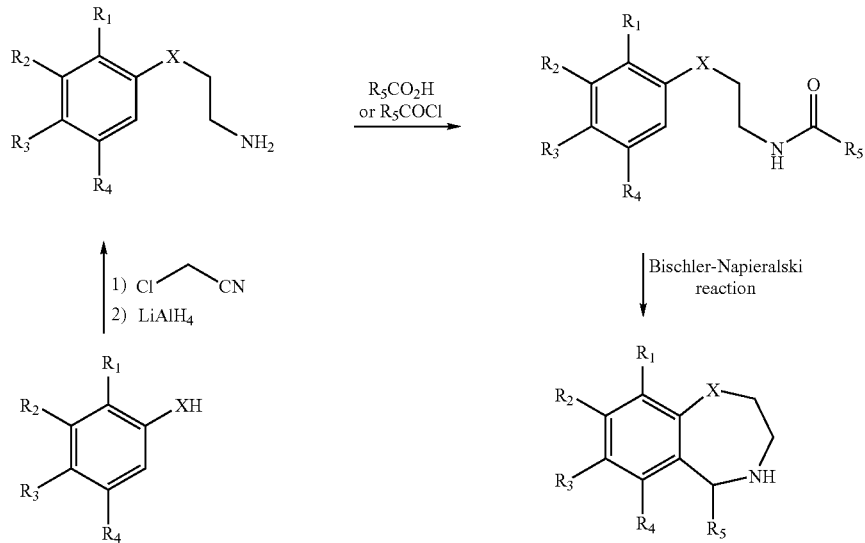

1,3,4,5-Tetrahydro-2H-1,4-benzodiazepin-2-one derivatives wherein X is $NR^{15}$, Y is CO and $R^6$ is hydrogen might be prepared by Friedel-Crafts acylation of the appropriate acetylated-aniline with the respective acyl chloride (Sternbach L. H. et al., *J. Org. Chem.* 1962, 27, 3781–3788), followed by N-deprotection-cyclisation by treatment with methyl esters of α-amino acids (Sternbach L. H. et al., *J. Org. Chem.* 1962, 27, 3788–3796) and finally hydrogenolysis of the dihydro compound (Fryer R. I. et al., *J. Med. Chem.* 1964, 386–389) (Scheme 4a). An alternative synthetic approach to such 1,3,4,5-tetrahydro-2H-1,4-benzodiazepin-2-one derivatives is described in Scheme 4b. According to this methodology, the arylketone derivative is obtained by Friedel-Crafts acylation and a subsequent nitration and hydrogenation led to the aniline derivative. The 1,3-dihydro-benzo[e][1,4]diazepin-2-one skeleton is then obtained according to a well-described cyclisation procedure involving bromoacetyl bromide and ammonia (Bock M. G. et al., *J. Org. Chem.* 1987, 3232–3239; Zhang W. et al., *J. Med. Chem.* 1994, 745–757). At this stage the amide can be N-alkylated and the 1,3,4,5-tetrahydro-2H-1,4-benzodiazepin-2-one derivative was finally obtained by hydride reduction (Gilman N. W. et al., *J. Am. Chem. Soc.* 1990, 3969–3978).

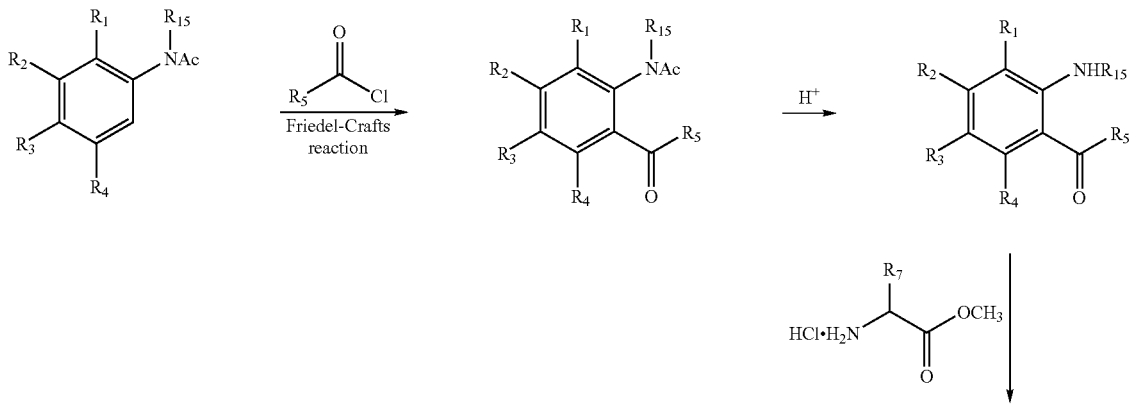

-continued

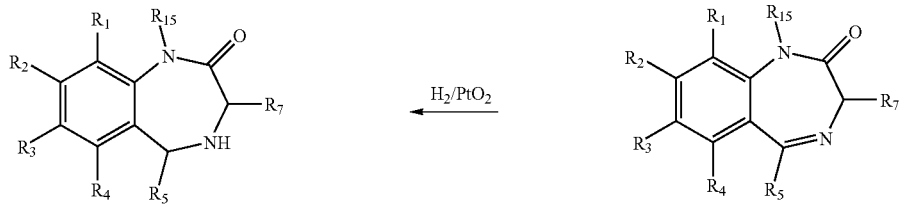

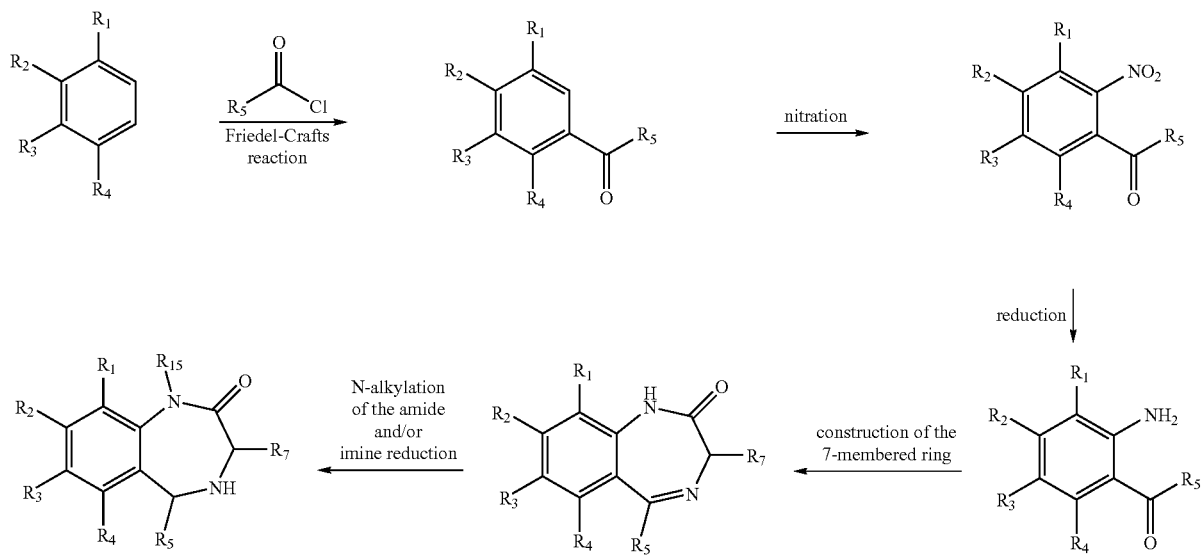

Scheme 4b

For the preparation of benzazepine derivatives with electron-withdrawing substituents on the phenyl ring, the previous procedures based on the Bischler-Napieralski reaction are incompatible. Therefore cyano groups might be introduced by reaction of a triflate with cyanide ions in the presence of palladium(0) (Austin N. E. et al., *Bioorg. Med. Chem. Lett.* 2000, 10, 2553–2555; Ritter K. et al., *Synthesis* 1993, 735; Selnick H. G. et al., *Synth. Commun.* 1995, 25, 20, 3255–3262) (Scheme 5).

Carboxylate groups might also be introduced by reaction of a triflate with carbon monoxide and an alcohol in the presence of palladium(0) (Roth G. P. et al., *Tetrahedron Lett.* 1992, 33, 1959; Ma D. et al., *Bioorg. Med. Chem. Lett.* 1998, 8, 18, 2447–2450; Fisher M. J. et al., *J. Med. Chem.* 1997, 40, 2085–2101; Kraus G. A. et al., *Tetrahedron Lett.* 1994, 35, 9189–9190). These carboxylate functions can subsequently be converted into amino functionalties by hydrolysis followed by Curtius reaction (Scheme 6).

Scheme 5

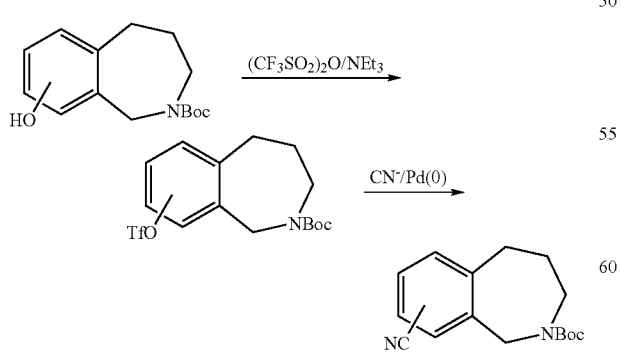

Scheme 6

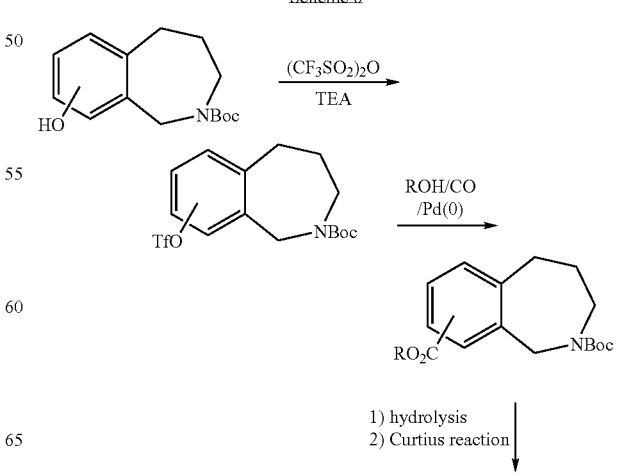

-continued

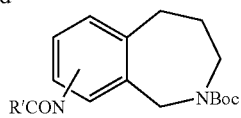

Halogen containing 2-benzazepines may be prepared by treatment of halogenated tetralone oximes with POCl$_3$/DMF and the resulting 1,3,4,5-tetrahydro-1-oxo-2H-2-benzazepine-2-carboxaldehydes can be subsequently deformylated and reduced (Majo V. J. et al., *Synth. Commun.* 1995, 25, 23, 3863–3868) (Scheme 7).

Scheme 7

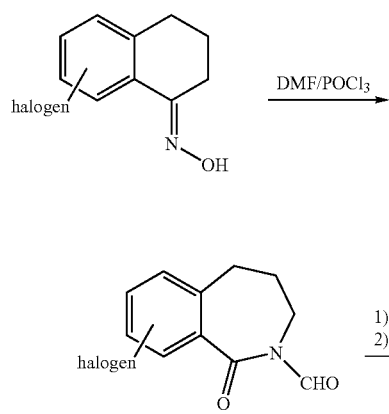

8-nitro-2,3,4,5-tetrahydro-1H-2-benzazepine might be prepared by regioselective nitration of 2,3,4,5-tetrahydro-1H-2-benzazepin-1-one using potassium nitrate and sulfuric acid (Grunewald G. L. et al., *J. Heterocyclic Chem.* 1994, 31, 1609–1617) (Scheme 8).

Scheme 8

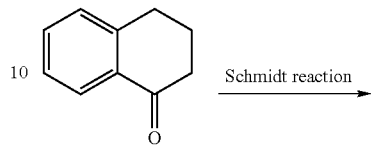

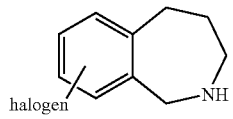

The preparation of enantiomerically pure 1-substituted-2-tetrahydrobenzazepine derivatives (Scheme 9) was based on a methodology described for the synthesis of optically pure 1-substituted tetrahydroisoquinolines (Polniaszek R. P. et al., *J. Am. Chem. Soc.* 1989, 111, 4859–4863). The key step of this asymmetric synthesis is a stereoselective hydride reduction of a chiral imminium ion obtained by Bischler-Napieralski reaction. The chirality resident in the substrate would be derived from the commercially available (S)-(−)-α-phenethylamine.

Scheme 9

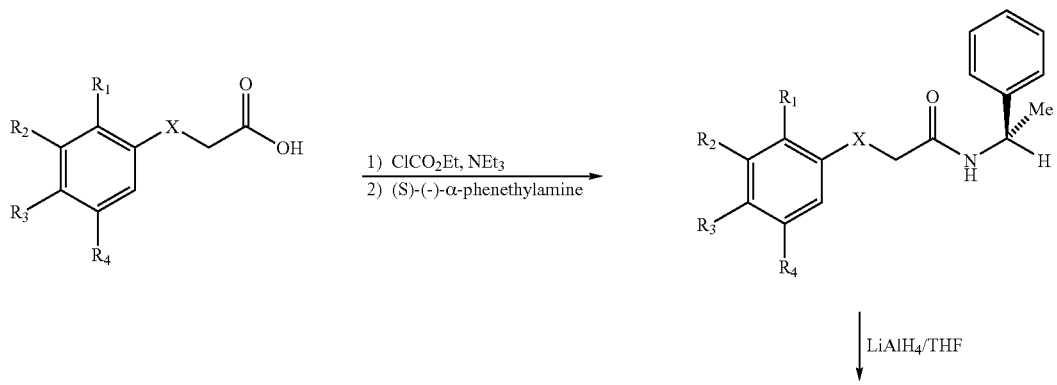

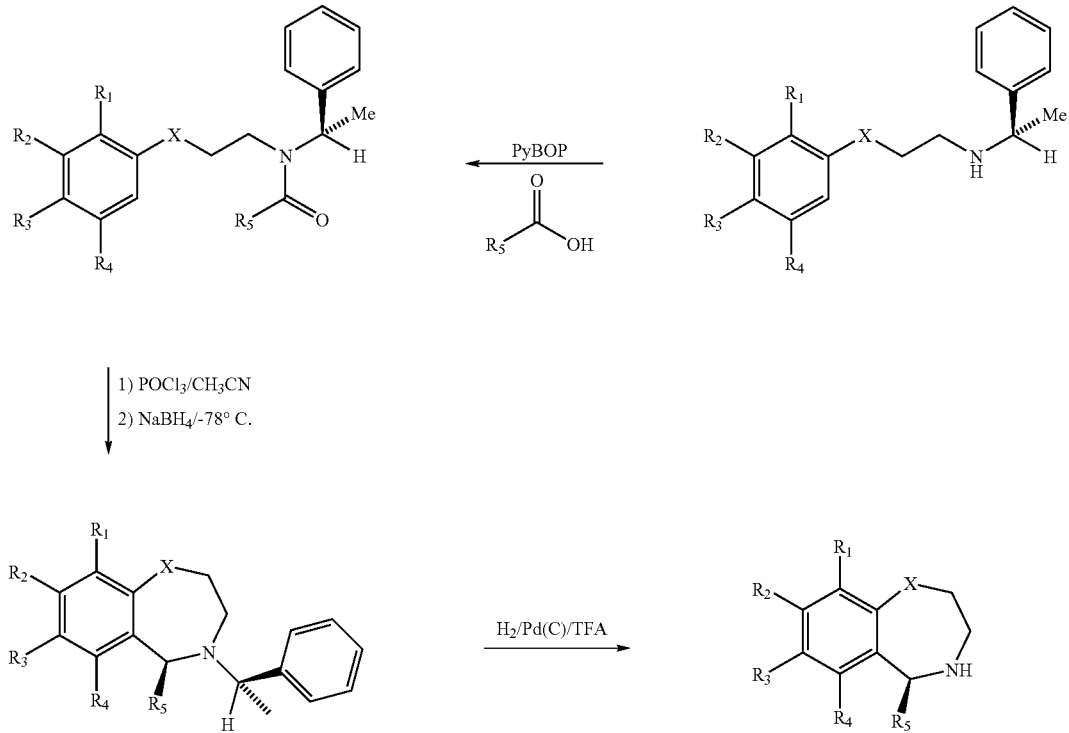

EXPERIMENTAL SECTION

Abbreviations

AcOEt Ethyl acetate
Bn Benzyl
Boc Tert-butoxycarbonyl
BSA Bovine serum albumine
CHO Chinese hamster ovary
DMF Dimethylformamide
DMSO Dimethylsulfoxide
ES Electron spray
FCS Foetal calf serum
FLIPR Fluorescent imaging plate reader
HBSS Hank's balanced salt solution
HEPES 4-(2-Hydroxyethyl)-piperazine-1-ethanesulfonic acid
HV High vacuum
MeOH Methanol
Min minute(s)
MS Mass spectroscopy
LC Liquid chromatography
PyBOP Benzotriazole-1-yl-oxy-tris-pyrrolidino-Phosphonium hexafluorophosphate
$R_f$ Retention front
rt retention time
RT Room temperature
TEA Triethylamine
TFA Trifluoroacetic acid
Tf $CF_3SO_2$—
THF Tetrahydrofuran
TLC Thin layer chromatography

I. Biology

Determination of $OX_1$ and $OX_2$ Receptor Antagonist Activities

The $OX_1$ and $OX_2$ receptor antagonist activities of the compounds of general formula (I) were determined in accordance with the following experimental method.

Experimental Method:

Intracellular Calcium Measurements

Chinese hamster ovary (CHO) cells expressing the human orexin-1 receptor and the human orexin-2 receptor, respectively, were grown in culture medium (Ham F-12 with L Glutamine) containing 300 μg/ml G418, 100 U/ml penicillin, 100 μg/ml streptomycin and 10% inactivated foetal calf serum (FCS).

The cells were seeded at 80'000 cells/well into 96-well black clear bottom sterile plates (Costar) which had been precoated with 1% gelatine in Hanks' Balanced Salt Solution (HBSS). All reagents were from Gibco BRL.

The seeded plates were incubated overnight at 37° C. in 5% $CO_2$.

Human orexin-A as an agonist was prepared as 1 mM stock solution in methanol:water (1:1), diluted in HBSS containing 0.1% BSA and 2 mM HEPES for use in the assay at a final concentration of 10 nM.

Antagonists were prepared as 10 mM stock solution in DMSO, then diluted in 96-well plates, first in DMSO, then in HBSS containing 0.1% bovine serum albumin (BSA) and 2 mM HEPES.

On the day of the assay, 100 μl of loading medium (HBSS containing 1% FCS, 2 mM HEPES, 5 mM probenecid (Sigma) and 3 μM of the fluorescent calcium indicator fluo-3 AM (1 mM stock solution in DMSO with 10% pluronic acid Molecular Probes)) was added to each well.

The 96-well plates were incubated for 60 min at 37° C. in 5% $CO_2$. The loading solution was then aspirated and cells were washed 3 times with 200 μl HBSS containing 2.5 mM probenecid, 0.1% BSA, 2 mM HEPES. 100 μl of that same buffer was left in each well.

Within the Fluorescent Imaging Plate Reader (FLIPR, Molecular Devices), antagonists were added to the plate in a volume of 50 μl, incubated for 20 min and finally 100 μl of agonist was added. Fluorescence was measured for each well at 1 second intervals, and the height of each fluorescence peak was compared to the height of the fluorescence peak induced by 10 nM orexin-A with buffer in place of antagonist. For each antagonist; $IC_{50}$ values (the concentration of compound needed to inhibit 50% of the agonistic response) were determined. Selected compounds are displayed in Table 1.

TABLE 1

|  | $IC_{50}$ (nM) | |
| --- | --- | --- |
|  | $OX_1$ | $OX_2$ |
| Example 3 | 99 | >10000 |
| Example 5 | 64 | 7900 |
| Example 9 | 23 | 1239 |
| Example 20 | 23 | 231 |
| Example 23 | 21 | 189 |
| Example 25 | 41 | 241 |
| Example 34 | 41 | 9192 |
| Example 35 | 32 | 7041 |
| Example 68 | 12 | 174 |
| Example 69 | 9 | 349 |

II. Chemistry

The following examples illustrate the preparation of pharmacologically active compounds of the invention but do not at all limit the scope thereof. All temperatures are stated in ° C. All hydrochloride salts were prepared by dissolving the free base in dichloromethane and treating the resulting solution with an excess of HCl in 2-propanol (5–6M).

A. Starting Materials: Synthesis of Tetrahydrobenzazepine and Related Heterocyclic Derivatives:

3-(3,4-Dimethoxy-phenyl)-propionamide

To a stirred solution of 3-(3,4-dimethoxy-phenyl)-propionic acid (10.0 g, 47.56 mmol) in dry THF (175 ml), under nitrogen, was added TEA (7.3 ml, 52.44 mmol), and the resulting mixture was cooled to −10° C. before ethyl chloroformate (5 ml, 52.47 mmol) was added dropwise. After stirring at −10° C. (20 min), ammonium hydroxide (25% in water, 105 ml) in THF (105 ml) was added and the mixture was stirred at −15° C. for 30 min and then at RT for 1.5 h. The reaction mixture was concentrated in vacuo, extracted three times with $CH_2Cl_2$ and the combined organic extracts were washed with saturated aqueous $NaHCO_3$ and brine. The organic phase was dried over anhydrous $MgSO_4$, filtered and concentrated to give the title compound (9.73 g, 46.50 mmol, 97%) as a colorless solid. No further purification of the crude amide was necessary.

LC-MS: rt=2.94 min, 210 (M+1, ES+).

3-(3,4-Dimethoxy-phenyl)-propylamine

A solution of 3-(3,4-dimethoxy-phenyl)--propionamide (11.09 g, 53.00 mmol) in anhydrous THF (400 ml) was slowly added to a stirred, ice-cooled suspension of $LiAlH_4$ (4.02 g, 106.00 mmol) in anhydrous THF (170 ml). Upon completion of the addition, the mixture was stirred at reflux for 2 h. After cooling to 0° C., $H_2O$ (5 ml) and NaOH 1N (5 ml) were added dropwise to decompose the excess of hydride. The suspension was then filtered and the residue after evaporation was partitioned between $H_2O$ (40 ml) and $CH_2Cl_2$ (100 ml). The organic layer was washed with saturated aqueous $NaHCO_3$ and brine, dried over anhydrous $MgSO_4$, and concentrated under reduced pressure to give the crude amine (7.00 g, 35.84 mmol, 68%) as a yellow oil.

$^1$H-NMR (300 MHz, $CDCl_3$) δ: 6.9–6.6 (3H, m), 3.9–3.8 (6H, d), 2.9–2.7 (2H, m), 2.65–2.55 (2H, m), 1.9–1.75 (2H, m).

2-(3,4-Dimethoxy-phenyl)-N-[3-(3,4-dimethoxy-phenyl)-propyl]-acetamide

A solution of 3-(3,4-dimethoxy-phenyl)-propylamine (12.51 g, 64.06 mmol) and TEA (10 ml, 71.84 mmol) in anhydrous THF (70 ml) was cooled to 0° C. and (3,4-dimethoxy-phenyl)-acetyl chloride (13.75 g, 64.07 mmol) in THF (28 ml) was added dropwise. After stirring at RT for 13 h under nitrogen, a saturated aqueous $NaHCO_3$ solution was added and the reaction mixture was extracted three times with AcOEt. The organic phase was dried over anhydrous $MgSO_4$, filtered and the solvent was removed in vacuo. A subsequent washing of the crude solid with toluene gave the title compound (12.81 g, 34.30 mmol, 53%) as a beige solid.

LC-MS: rt=4.00 min, 374 (M+1, ES+).

1-(3,4-Dimethoxy-benzyl)-7,8-dimethoxy-2,3,4,5-tetrahydro-1H-benzo[c]azepine

A mixture of 2-(3,4-dimethoxy-phenyl)-N-[3-(3,4-dimethoxy-phenyl)-propyl]-acetamide (6.16 g, 16.49 mmol) and $POCl_3$ (4.95 ml, 54.07 mmol) in anhydrous acetonitrile (185 ml) was stirred at reflux for 4 h under nitrogen. After cooling, the reaction mixture was concentrated in vacuo and the residue was dissolved in MeOH (125 ml). The solution was cooled to 0° C. and $NaBH_4$ (4.31 g, 113.93 mmol) was added portionwise. After stirring at 0° C. for 2 h under nitrogen, the reaction mixture was poured into $H_2O$ and extracted three times with $CH_2Cl_2$. The combined organic extracts were washed with brine, dried over anhydrous $MgSO_4$, filtered and concentrated to give a crude oil. Flash chromatography ($CH_2Cl_2$/MeOH: 9/1) gave the title compound as a racemic mixture (2.29 g, 6.40 mmol, 39%, yellow oil).

LC-MS: rt=3.02 min, 358 (M+1, ES+).

[1-(3,4-Dimethoxy-benzyl)-7,8-dimethoxy-1,3,4,5-tetrahydro-benzo[c]azepin-2-yl]-phenyl-acetic acid methyl ester A mixture of 1-(3,4-dimethoxy-benzyl)-7,8-dimethoxy-2,3,4,5-tetrahydro-1H-benzo[c]azepine (1.10 g, 3.08 mmol), TEA (1.3 ml, 9.33 mmol), and methyl α-bromophenylacetate (487 μl, 3.09 mmol) in anhydrous toluene (13 ml) was stirred at reflux for 17 h under nitrogen. After cooling, the reaction mixture was dissolved in $CH_2Cl_2$ (40 ml), washed with $H_2O$ (15 ml), and the aqueous phase was extracted twice with $CH_2Cl_2$. The combined organic phases were dried over anhydrous $MgSO_4$, filtered and concentrated to give a crude oil. Flash chromatography (AcOEt/hexane: 1/1) gave the title compound as a mixture of stereoisomers (1.34 g, 2.65 mmol, 86%, yellow oil).

LC-MS: rt=3.99 min. and rt=4.24 min (diastereoisomers), 506 (M+1, ES+).

[1-(3,4-Dimethoxy-benzyl)-7,8-dimethoxy-1,3,4,5-tetrahydro-benzo[c]azepin-2-yl]-phenyl-acetic acid To a solution of [1-(3,4-dimethoxy-benzyl)-7,8-dimethoxy-1,3,4,5-tetrahydro-benzo[c]azepin-2-yl]-phenyl-acetic acid methyl ester (1.17 g, 2.31 mmol), in MeOH (9 ml) and dioxane (12 ml), was added dropwise aqueous NaOH 2N (11 ml, 22 mmol). The resulting yellow homogeneous mixture was then stirred at 45° C. for 8 h. The reaction mixture was then concentrated in vacuo and washed with Et$_2$O (5 ml). The aqueous phase was acidified (pH=1) with HCl 2N and extracted three times with CH$_2$Cl$_2$. The combined organic phases were dried over anhydrous MgSO$_4$, filtered and concentrated to give the titled carboxylic acid (1.14 g, 2.31 mmol, 100%) as a beige solid (mixture of diastereoisomers).

LC-MS: rt=3.58 min, 492 (M+1, ES+).

3-(4-Benzyloxy-3-methoxy-phenyl)-propionic acid benzyl ester

A mixture of 3-(4-hydroxy-3-methoxy-phenyl)-propionic acid (5.1 g, 25.99 mmol), anhydrous K$_2$CO$_3$ (25 g, 180.88 mmol) and benzyl bromide (7.5 ml, 63.14 mmol) in anhydrous acetone (100 ml) was stirred at reflux for 7.5 h under nitrogen. After cooling, the reaction mixture was filtered and concentrated in vacuo. Flash chromatography (CH$_2$Cl$_2$) gave the title compound (8.83 g, 23.45 mmol, 90%).

LC-MS: rt=5.65 min, 377 (M+1, ES+).

3-(4-Benzyloxy-3-methoxy-phenyl)-propionic acid

To a solution of-3-(4-benzyloxy-3-methoxy-phenyl)-propionic acid benzyl ester (11.03 g, 29.30 mmol), in MeOH (110 ml) and dioxane (145 ml), was added dropwise aqueous NaOH 2N (139 ml, 278 mmol). The resulting yellow homogeneous mixture was then stirred at 50° C. for 17 h. The reaction mixture was then concentrated in vacuo and washed with Et$_2$O (100 ml). The aqueous phase was acidified (pH=1) with HCl 2N and extracted three times with CH$_2$Cl$_2$. The combined organic phases were dried over anhydrous MgSO$_4$, filtered and concentrated to give the title carboxylic acid (8.4 g, 29.30 mmol, 100%) as a colorless solid.

LC-MS: rt=4.53 min, 285 (M-1, ES-).

3-(4-Benzyloxy-3-methoxy-phenyl)-propionamide

To a stirred solution of 3-(4-benzyloxy-3-methoxy-phenyl)-propionic acid (8.38 g, 29.30 mmol) in dry THF (110 ml), under nitrogen, was added TEA (4.5 ml, 32.33 mmol), and the resulting mixture was cooled to −10° C. before ethyl chloroformate (3.1 ml, 32.53 mmol) was added dropwise. After stirring at −10° C. (20 min), ammonium hydroxide (25% in water, 65 ml) in THF (65 ml) was added and the mixture was stirred at −15° C. for 30 min and then at RT for 1.5 h. The reaction mixture was concentrated in vacuo, extracted three times with CH$_2$Cl$_2$ and the combined organic extracts were washed with saturated aqueous NaHCO$_3$ and brine. The organic phase was dried over anhydrous MgSO$_4$, filtered and concentrated to give the title compound (8.40 g, 29.30 mmol, 100%) as a colorless solid. No further purification of the crude amide was necessary.

LC-MS: rt=4.08 min, 286 (M+1, ES+).

3-(4-Benzyloxy-3-methoxy-phenyl)-propylamine

A solution of 3-(4-benzyloxy-3-methoxy-phenyl)-propionamide (7.85 g, 27.53 mmol) in anhydrous THF (210 ml) was slowly added to a stirred, ice-cooled suspension of LiAlH$_4$ (2.09 g, 55.07 mmol) in anhydrous THF (90 ml). Upon completion of the addition, the mixture was stirred at reflux for 1 h. After cooling to 0° C., H$_2$O (15 ml) was added dropwise to decompose the excess of hydride, and the resulting suspension was then filtered. The residue after evaporation was partitioned between H$_2$O (50 ml) and CH$_2$Cl$_2$ (100 ml). The organic layer was washed with NaHCO$_3$ and brine, dried over anhydrous MgSO$_4$, and concentrated under reduced pressure to give the crude. amine (6.03 g, 22.22 mmol, 81%) as a yellow oil.

LC-MS: rt=3.20 min, 272 (M+1, ES+).

N-[3-(4-Benzyloxy-3-methoxy-phenyl)-propyl]-2-(3,4-dimethoxy-phenyl)-acetamide

A solution of 3-(4-benzyloxy-3-methoxy-phenyl)-propylamine (6.06 g, 22.36 mmol) and TEA (3.5 ml, 25.14 mmol) in anhydrous THF (25 ml) was cooled to 0° C. and (3,4-dimethoxy-phenyl)-acetyl chloride (4.80 g, 22.36 mmol) in THF (10 ml) was added dropwise. After stirring at RT for 28 h under nitrogen, a saturated aqueous NaHCO$_3$ solution was added and the reaction mixture was extracted three times with AcOEt. The organic phase was dried over anhydrous MgSO$_4$, filtered and the solvent was removed in vacuo. A subsequent washing of the crude solid with toluene gave the title compound (6.57 g, 14.61 mmol, 65%) as a beige solid.

LC-MS: rt=4.90 min, 450 (M+1, ES+).

8-Benzyloxy-1-(3,4-dimethoxy-benzyl)-7-methoxy-2,3,4,5-tetrahydro-1H benzo[c]azepine A mixture of N-[3-(4-benzyloxy-3-methoxy-phenyl)-propyl]-2-(3,4-dimethoxy-phenyl)-acetamide (6.04 g, 13.43 mmol) and POCl$_3$ (4.1 ml, 44.78 mmol) in anhydrous acetonitrile (350 ml) was stirred at reflux for 5 h under nitrogen. After cooling, the reaction mixture was concentrated in vacuo and the residue was dissolved in MeOH (120 ml). The solution was cooled to 0° C. and NaBH$_4$ (3.50 g, 92.70 mmol) was added portionwise. After stirring at 0° C. for 2 h under nitrogen, the reaction mixture was poured into H$_2$O and extracted three times with CH$_2$Cl$_2$. The combined organic extracts were washed with brine, dried over anhydrous MgSO$_4$, filtered and concentrated to give a crude oil. Flash chromatography (CH$_2$Cl$_2$/MeOH: 9/1) gave the title compound as a racemic mixture (2.44 g, 5.62 mmol, 42%, yellow oil).

LC-MS: rt=3.52 min, 434 (M+1, ES+).

(3,4-Dimethoxy-phenoxy)-acetonitrile

To a solution of 3,4-dimethoxyphenol (5.0 g, 32.4 mmol) in dry acetone (160 ml), were added chloroacetonitrile (2.05 ml, 32.4 mmol) and anhydrous K$_2$CO$_3$ (6.72 g, 48.6 mmol). The reaction mixture was stirred at reflux for 20 h under nitrogen. After cooling, the mixture was filtered and concentrated in vacuo. The residue was combined with H$_2$O, extracted with CH$_2$Cl$_2$, and the combined organic phases were dried over anhydrous MgSO$_4$, filtered and concentrated to give a crude oil. Flash chromatography (AcOEt/hexane: 3/7) gave the title product (4.5 g, 68%).

$^1$H-NMR (300 MHz, CDCl$_3$) δ: 6.8 (1H, d), 6.6 (1H, d), 6.5 (1H, dd), 4.75 (2H, s), 3.35 (6H, d).

2-(3,4-Dimethoxy-phenoxy)-ethylamine

To a cold (0° C.) suspension of LiAlH$_4$ (1.73 g, 45.6 mmol) in anhydrous THF (72 ml), was added dropwise a solution of (3,4-dimethoxy-phenoxy)-acetonitrile (5.88 g, 30.4 mmol) in anhydrous THF (42 ml). The resulting mixture was allowed to warm-up and stirred at RT for 20 h under nitrogen. The reaction mixture was combined with a mixture of H$_2$O/2N NaOH$_{(aq)}$ (4/1) to destroy the excess of LiAlH$_4$. The white suspension was filtered and the solid was washed with CH$_2$Cl$_2$. The combined organic phases were dried over anhydrous MgSO$_4$, filtered and concentrated to give a crude oil. Flash chromatography (CH$_2$Cl$_2$/MeOH: 9/1) gave the title product (4.65 g, 77%).

$^1$H-NMR (300 MHz, CDCl$_3$) δ: 6.78 (1H, d), 6.55 (1H, d), 6.4 (1H, dd), 3.95 (2H, t), 3.80 (6H, d), 3.05 (2H, t), 1.92 (2H, br·s.).

N-[2-(3,4-Dimethoxy-phenoxy)-ethyl]-2-(3,4-dimethoxy-phenyl)-acetamide

To a cold (0° C.) solution of 2-(3,4-dimethoxy-phenoxy)-ethylamine (2.3 g, 11.8 mmol) in anhydrous THF (21 ml), were added TEA (1.4 ml, 19.2 mmol) and portionwise 3,4-dimethoxyphenylacetylchloride (2.49 g, 11.6 mmol). The resulting mixture was stirred at RT for 20 h under nitrogen. The mixture was combined with H$_2$O and extracted three times with CH$_2$Cl$_2$. The combined organic phases were dried over anhydrous MgSO$_4$, filtered and concentrated to give a crude solid. Recrystallisation from diethylether gave the title product (3.59 g, 80%) as a white solid.

$^1$H-NMR (300 MHz, CDCl$_3$) δ: 6.8 (3H, m), 6.4 (1H, d), 6.35 (1H, dd), 5.95 (1H, br·s) 3.95 (2H, t), 3.80 (12H, q), 3.6 (2H, m), 3.55 (2H, s).

LC-MS: rt=3.84 min, 376 (M+1, ES+).

5-(3,4-Dimethoxy-benzyl)-7,8-dimethoxy-2,3,4,5-tetrahydro benzo[f][1,4]oxazepine To a stirred solution of N-[2-(3,4-dimethoxy-phenoxy)-ethyl]-2-(3,4-dimethoxy-phenyl)-acetamide (3.6 g, 9.56 mmol) in dry CH$_3$CN (20 ml), was added POCl$_3$ (2.62 ml, 28.6 mmol). The resulting mixture was stirred at reflux for 3 h under nitrogen. After cooling, the reaction mixture was concentrated in vacuo and the residue was dissolved in MeOH (80 ml). The solution was cooled to 0° C. and NaBH$_4$ (2.53 g, 67.0 mmol) was added portionwise. The resulting pale yellow suspension was stirred at RT for 16 h under nitrogen. The reaction mixture was poured into H$_2$O and extracted three times with CH$_2$Cl$_2$. The combined organic phases were dried over anhydrous MgSO$_4$, filtered and concentrated to give a crude oil. Flash chromatography (CH$_2$Cl$_2$/MeOH: 9/1) gave the title product (1.14 g, 33%) as a viscous brown oil.

$^1$H-NMR (300 MHz, CDCl$_3$) δ: 6.8–6.6 (5H, m), 6.45 (1H, s), 4.15 (1H, m), 3.80 (12H, q), 3.55–2.95 (6H, m).

LC-MS: rt=2.99 min, 360 (M+1, ES+).

(3,4-Dimethoxy-phenylsulfanyl)-acetonitrile

To a solution of 3,4-dimethoxythiophenol (5.0 g, 29.4 mmol) in dry DMF (150 ml), were added chloroacetonitrile (1.85 ml, 29.4 mmol), anhydrous K$_2$CO$_3$ (6.09 g, 44.1 mmol) and DMAP (358 mg, 2.9 mmol). The reaction mixture was stirred at 80° C. for 20 h under nitrogen. After cooling, the mixture was filtered and concentrated in vacuo. The residue was combined with H$_2$O, extracted with CH$_2$Cl$_2$, the combined organic phases were dried over anhydrous MgSO$_4$, filtered and concentrated to give a crude oil. Flash chromatography (AcOEt) gave the title product (5.16 g, 84%).

$^1$H-NMR (300 MHz, CDCl$_3$) δ: 7.2 (1H, d), 7.15 (1H, d), 6.9 (1H, d), 3.85 (6H, d), 3.5 (2H, s).

2-(3,4-Dimethoxy-phenylsulfanyl)-ethylamine

To a cold (0° C.) solution of (3,4-dimethoxy-phenylsulfanyl)-acetonitrile (7.53 g, 36.0 mmol) in anhydrous THF (41 ml), was added portionwise NaBH$_4$ (1.22 g, 32.0 mmol) and dropwise a solution of BF$_3$.OEt$_2$ (5.37 ml, 20.0 mmol) in anhydrous THF (13.4 ml) over 30 min. The resulting mixture was stirred at RT for 3 h under nitrogen. The mixture was concentrated in vacuo, the residue was dissolved in CH$_2$Cl$_2$ and washed with HCl 37%. The aqueous phase was neutralized with NaOH 30% and extracted with CH$_2$Cl$_2$. The combined organic phases were dried over anhydrous MgSO$_4$, filtered and concentrated to give a crude oil. Flash chromatography (CH$_2$Cl$_2$/MeOH: 9/1) gave the title product (3.6 g, 46%).

$^1$H-NMR (300 MHz, CDCl$_3$) δ: 7.05 (2H, m), 6.85 (1H, d), 3.80 (6H, d), 2.95 (2H, m), 1.7 (2H, br·s.).

2-(3,4-Dimethoxy-phenyl)-N-[2-(3,4-dimethoxy-phenylsulfanyl)-ethyl]-acetamide

To a cold (0° C.) solution of 2-(3,4-dimethoxy-phenylsulfanyl)-ethylamine (3.97 g, 18.6 mmol) in anhydrous THF (49 ml), were added TEA (3.11 ml, 18.6 mmol) and portionwise 3,4-dimethoxyphenylacetylchloride (4.0 g, 18.6 mmol). The resulting mixture was stirred at RT for 20 h under nitrogen. The mixture was combined with H$_2$O and extracted three times with CH$_2$Cl$_2$. The combined organic phases were dried over anhydrous MgSO$_4$, filtered and concentrated to give a crude solid. Flash chromatography (AcOEt) gave the title product (7.08 g, 97%).

$^1$H-NMR (300 MHz, CDCl$_3$) δ: 6.95–6.7 (6H,m), 5.95 (1H,br·s), 3.95 (12H,q), 3.5 (2H,s), 3.55 (2H,q), 2.95 (2H,t).

LC-MS: rt=3.87 min, 392 (M+1, ES+).

9-(3,4-Dimethoxy-benzyl)-2,3-dimethoxy-6,7,8,9-tetrahydro-5-thia-8-aza-benzocycloheptene To a stirred solution of 2-(3,4-dimethoxy-phenyl)-N-[2-(3,4-dimethoxy-phenylsulfanyl)-ethyl]-acetamide (4.0 g, 10.0 mmol) in dry CH$_3$CN (21 ml), was added POCl$_3$ (2.80 ml, 30.0 mmol). The resulting mixture was stirred at reflux for 3 h under nitrogen. After cooling, the reaction mixture was concentrated in vacuo and the residue was dissolved in MeOH (85 ml). The solution was cooled to 0° C. and NaBH$_4$ (2.7 g, 69.0 mmol) was added portionwise, the resulting pale yellow suspension was stirred at RT for 16 h under nitrogen. The reaction mixture was poured into H$_2$O and extracted three times with CH$_2$Cl$_2$. The combined organic phases were dried over anhydrous MgSO$_4$, filtered and concentrated to give a crude oil. Flash chromatography (CH$_2$Cl$_2$/MeOH: 9/1) gave the title product (1.14 g, 27%) as a viscous brown oil.

$^1$H-NMR (300 MHz, CDCl$_3$) δ: 7.1 (1H, s), 6.8 (4H, s), 4.6 (1H, m), 4.15, 3.80 (12H, q), 3.45–2.75 (6H, m).

LC-MS: rt=4.39 min, 376 (M+1, ES+).

9-(3,4-Dimethoxy-benzyl)-2,3-dimethoxy-6,7-dihydro-9H-5-thia-8-aza-benzocycloheptene-8-carboxylic acid tert-butyl ester To a cold (0° C.) stirred solution of 9-(3,4-dimethoxy-benzyl)-2,3-dimethoxy-6,7,8,9 tetrahydro-5-thia-8-aza-benzocycloheptene (417 mg, 1.11 mmol) in dry CH$_2$Cl$_2$ (5 ml), were added TEA (168 μL, 1.2 mmol) and di-tert.-butyl-dicarbonate (262 mg, 1.2 mmol). The resulting mixture was allowed to warm-up and stirred at RT for 20 h under nitrogen. The reaction mixture was combined with water, extracted twice with CH$_2$Cl$_2$, the combined organic phases were dried over anhydrous MgSO$_4$, filtered and concentrated to give a crude yellow oil. Flash chromatography (AcOEt) gave the title compound as a pale yellow oil (486 mg, 91%).

$^1$H-NMR (300 MHz, CDCl$_3$) δ: 7.15 (1H, d); 6.6–6.8 (4H, m); 5.05 (1H, m); 3.85 (12H, d); 3.65 (2H, m); 3.45 (2H, m); 2.75 (2H, m); 1.45 (9H, d).

9-(3,4-Dimethoxy-benzyl)-2,3-dimethoxy-5,5-dioxo-5,6,7,9-tetrahydro-5λ$^6$-thia-8-aza-benzocycloheptene-8-carboxylic acid tert-butyl ester To a cold (0° C.) stirred solution of 9-(3,4-dimethoxy-benzyl)-2,3-dimethoxy-6,7-dihydro 9H-5-thia-8-aza-benzocycloheptene-8-carboxylic acid tert-butyl ester (100 mg, 0.21 mmol) in dry CH$_2$Cl$_2$ (1 ml), was added 3-chloroperbenzoic acid (106 mg, 0.614 mmol). The resulting mixture was stirred at 0° C. for 2 h and allowed to warm-up and stirred at RT overnight. The reaction mixture was combined with water, extracted twice with CH$_2$Cl$_2$, the combined organic phases were dried over anhydrous MgSO$_4$, filtered and concentrated to give a crude oil. Flash chromatography (AcOEt/hexane: 1/1) gave the title compound as a pale yellow solid (76 mg, 71%).

$^1$H-NMR (300 MHz, CDCl$_3$) δ: 7.15 (1H, d); 6.6–6.8 (4H, m); 5.25 (1H, m); 3.85 (12H, d); 3.65 (2H, m); 3.35 (2H, m); 2.75 (2H, m); 1.35 (9H, d).

9-(3,4-Dimethoxy-benzyl)-2,3-dimethoxy-6,7,8,9-tetrahydro-5-thia-8-aza-benzocycloheptene 5,5-dioxide.

To a stirred solution of 9-(3,4-dimethoxy-benzyl)-2,3-dimethoxy-5,5-dioxo-5,6,7,9 tetrahydro-5λ$^6$-thia-8-aza-benzocycloheptene-8-carboxylic acid tert-butyl ester (310 mg, 0.61 mmol) in dry CH$_2$Cl$_2$ (3 ml), was added trifluoroacetic acid (372 μL, 4.86 mmol). The resulting mixture was stirred at RT for 20 h under nitrogen. The reaction mixture was combined with water/NaOH 2N, extracted twice with CH$_2$Cl$_2$, and the combined organic phases were dried over anhydrous MgSO$_4$, filtered and concentrated to give a crude oil. Flash chromatography (CH$_2$Cl$_2$/MeOH: 9/1) gave the title compound as a pale yellow oil (118 mg, 47%).

$^1$H-NMR (300 MHz, CDCl$_3$) δ: 7.6 (1H, d); 6.85 (4H, m); 4.95 (1H, m); 3.95–3.81 (12H, m); 3.45 (4H, m); 3.25 (2H, m).

2-(3,4-Dichloro-phenyl)-1-(3,4-dimethoxy-phenyl)-ethanone

A mixture of (3,4-dichloro-phenyl)-acetic acid (11.14 g, 54.33 mmol) and anhydrous DMF (1.45 ml) in thionyl chloride (137 ml) was stirred at RT, under nitrogen, for 17 h. The excess of thionyl chloride was removed under vacuum. Anhydrous toluene was added to the residue, which was again concentrated in vacuum (repeated two more times). Powdered anhydrous aluminium chloride (11.57 g, 86.72 mmol) was added portionwise (exothermic reaction) to a stirred mixture of 1,2-dimethoxy-benzene (6.92 ml, 54.34 mmol) and the previous acyl chloride in anhydrous dichloromethane (120 ml). An exothermic reaction occurred and the reaction mixture was heated at reflux for 2 h. The reaction mixture was allowed to cool to RT and was then poured into a mixture of ice (67 g) and aqueous 7.5N HCl (64 ml). The layers were separated and the aqueous layer was extracted with dichloromethane. The combined organic extracts were washed with brine, dried over magnesium sulfate, filtered and evaporated to dryness to give a brown residue (oil and solid). After a further drying (HV), anhydrous diethylether was added and a beige solid precipitated. The beige solid was filtered and further dried (8.33 g, 47%).

LC-MS: rt=5.25 min, 326 (M+1, ES+).

2-(3,4-Dichloro-phenyl)-1-(4,5-dimethoxy-2-nitro-phenyl)-ethanone

A heterogeneous mixture of 2-(3,4-dichloro-phenyl)-1-(3,4-dimethoxy-phenyl)-ethanone (8.33 g, 25.6 mmol) in acetic anhydride (65 ml) was added dropwise to a cooled (0° C.) solution of 65% nitric acid (140 ml) and acetic anhydride (21.3 ml). The resulting mixture was stirred at 0° C. for 2 h. Water was added dropwise and the resulting heterogeneous mixture was allowed to stir and warm-up slowly. The crude was then filtered and the beige solid was washed several times with distilled water and dried under HV (6.98 g, 74%).

LC-MS: rt=5.43 min, 370 (M+1, ES+).

1-(2-Amino4,5-dimethoxy-phenyl)-2-(3,4-dichloro-phenyl)-ethanone

To a mixture of 2-(3,4-dichloro-phenyl)-1-(4,5-dimethoxy-2-nitro-phenyl)-ethanone (9.62 g, 25.98 mmol) and palladium on charcoal (2.88 g, 30% in mass) was added dropwise methanol (500 ml) and the resulting heterogeneous mixture was hydrogenated (1 atm) at RT for 4 days. The reaction mixture was filtered over celite, and the celite cake was washed several times with anhydrous methanol. The filtrate was then evaporated to dryness and the crude brown oil was purified by flash chromatography (dichloromethane/methanol, 360/1) to give the expected aniline derivative as a brown oil (5.04 g, 57%).

LC-MS: rt=5.12 min, 341 (M+1, ES+).

2-Bromo-N-{2-[2-(3,4-dichloro-phenyl)-acetyl]-4,5-dimethoxy-phenyl}-acetamide 1-(2-Amino-4,5-dimethoxy-phenyl)-2-(3,4-dichloro-phenyl)-ethanone (5.52 g, 16.24 mmol) was dissolved in dichloromethane (20 ml), distilled water was then added (2 ml) and the resulting solution was cooled at −5° C. under nitrogen. Bromoacetylbromide (1.63 ml, 18.68 mmol) was dissolved in dichloromethane (10 ml) and added dropwise to the previous solution; the temperature was not allowed to exceed +5° C. The reaction mixture was stirred at 0° C. for 15 min and then allowed to reach the RT before further stirring for 2.5 h. Dichloromethane was added (30 ml) and the organic layer was washed with distilled water, saturated NaHCO$_3$ solution, and brine. It was dried over magnesium sulfate, filtered and the solvent was removed under vacuum. This crude mixture was purified by flash chromatography (dichloromethane/methanol, 360/1) to give the product as a yellow solid (5.25 g, 70%).

LC-MS: rt=5.65 min, 462 (M+1, ES+).

5-(3,4-Dichloro-benzyl)-7,8-dimethoxy-1,3-dihydro-benzo[e][1,4]diazepin-2-one

2-Bromo-N-{2-[2-(3,4-dichloro-phenyl)-acetyl]-4,5-dimethoxy-phenyl}-acetamide (5.25 g, 11.39 mmol) was placed at −10° C. under nitrogen. Ammonia in methanol (7N, 55 ml) was added dropwise at −10° C. and the reaction mixture was heated at 40° C. for 2.5 h, and then at reflux (75° C.) for 1 h. The solvent was evaporated under vacuum yielding a yellow solid which was dissolved in dichloromethane and washed with water. The organic phase was dried over magnesium sulfate, filtered and evaporated to dryness. Flashchromatography (dichloromethane/methanol, 18/1) yielded the expected product as a yellow solid (1.5 g, 35%).

LC-MS: rt=3.15 min, 380 (M+1, ES+).

5-(3,4-Dichloro-benzyl)-7,8-dimethoxy-1,3,4,5-tetrahydro-benzo[e][1,4]diazepin-2-one A solution of 5-(3,4-dichloro-benzyl)-7,8-dimethoxy-1,3-dihydro-benzo[e][1,4]diazepin-2-one (0.48 g, 1.17 mmol) in glacial acetic acid (1.67 ml) and methanol (9.4 ml) was stirred at 0° C. under nitrogen. Sodium cyanoborohydride (0.148 g, 2.23 mmol) was added portionwise and the reaction mixture was stirred at 0° C. for 30 min, and then at RT for 2 h. Water (17 ml) was added dropwise and the product was extracted with dichloromethane, washed with aqueous 1N ammonia. The organic phase was dried over magnesium sulfate, filtered and the solvent was removed under vacuum. The resulting yellow oil crystallized under HV (0.19 g, 41%).

LC-MS: rt=3.55 min, 382 (M+1, ES+).

B. General Procedure A:

At −15° C., a solution of the respective amine R$_9$R$_{10}$NH (1 equivalent) in THF (0.40 M) was added dropwise to a solution of 2-bromoacetyl bromide (1 equivalent) in THF (0.20 M). The reaction mixture was then treated dropwise with a solution of diisopropylethylamine (4 equivalents) in THF (2.0 M), allowed to warm up slowly to RT (in 30 min) and stirred at RT for 30 min. A solution of the respective benzazepine (1 equivalent) in THF (0.20 M) was added and the mixture was stirred at 75° C. for 15 h. After cooling, AcOEt and H$_2$O were added, and the aqueous phase was extracted twice with AcOEt. The combined organic extracts were washed with brine, dried over anhydrous MgSO$_4$, filtered and concentrated in vacuo. Flash chromatography yielded the expected benzazepine derivative.

EXAMPLE 1

2-[1-(3,4-Dimethoxy-benzyl)-7,8-dimethoxy-1,3,4,5-tetrahydro-benzo[c]azepin-2-yl]-N-naphthalen-1-ylmethyl-acetamide prepared by reaction of 2-bromoacetyl bromide with 1-naphtalenemethylamine and 1-(3,4-dimethoxy-benzyl)-7,8-dimethoxy-2,3,4,5-tetrahydro-1H-benzo[c]azepine.

LC-MS: rt=3.95 min, 555 (M+1, ES+).

EXAMPLE 2

N-Benzo[1,3]dioxol-5-ylmethyl-2-[1-(3,4-dimethoxy-benzyl)-7,8-dimethoxy-1,3,4,5-tetrahydro-benzo[c]azepin-2-yl]-acetamide prepared by reaction of 2-bromoacetyl bromide with piperonylamine and 1-(3,4-dimethoxy-benzyl)-7,8-dimethoxy-2,3,4,5-tetrahydro-1H-benzo[c]azepine.

LC-MS: rt=3.67 min, 549 (M+1, ES+).

EXAMPLE 3

2-[1-(3,4-Dimethoxy-benzyl)-7,8-dimethoxy-1,3,4,5-tetrahydro-benzo[c]azepin-2-yl]-N-indan-2-yl-acetamide prepared by reaction of 2-bromoacetyl bromide with 2-aminoindane hydrochloride and 1-(3,4-dimethoxy-benzyl)-7,8-dimethoxy-2,3,4,5-tetrahydro-1H-benzo[c]azepine.

LC-MS: rt=3.83 min, 531 (M+1, ES+).

EXAMPLE 4

2-[5-(3,4-Dimethoxy-benzyl)-7,8-dimethoxy-2,3-dihydro-5H-benzo[f][1,4]oxazepin-4-yl]-N-indan-2-yl-acetamide prepared by reaction of 2-bromoacetyl bromide with 2-aminoindane hydrochloride and 5-(3,4-dimethoxy-benzyl)-7,8-dimethoxy-2,3,4,5-tetrahydro-benzo[f][1,4]oxazepine.

LC-MS: rt=4.34 min, 533 (M+1, ES+).

EXAMPLE 5

2-[5-(3,4-Dimethoxy-benzyl)-7,8-dimethoxy-2,3-dihydro-5H-benzo[f][1,4]oxazepin-4-yl]-N-indan-1-yl-acetamide prepared by reaction of 2-bromoacetyl bromide with rac-1-aminoindane and 5-(3,4-dimethoxy-benzyl)-7,8-dimethoxy-2,3,4,5-tetrahydro-benzo[f][1,4]oxazepine.

LC-MS: rt=4.62 min, 533 (M+1, ES+).

EXAMPLE 6

2-[1-(3,4-Dimethoxy-benzyl)-7,8-dimethoxy-1,3,4,5-tetrahydro-benzo[c]azepin-2-yl]-N-indan-1-yl-acetamide prepared by reaction of 2-bromoacetyl bromide with rac-1-aminoindane and 1-(3,4-dimethoxy-benzyl)-7,8-dimethoxy-2,3,4,5-tetrahydro-1H-benzo[c]azepine.

LC-MS: rt=3.90 min, 531 (M+1, ES+).

EXAMPLE 7

2-[9-(3,4-Dimethoxy-benzyl-2,3-dimethoxy-5,5-dioxo-5,6,7,9-tetrahydro-5λ$^6$-thia-8-aza-benzocyclohepten-8-yl]-N-indan-2-yl-acetamide prepared by reaction of 2-bromoacetyl bromide with 2-aminoindane hydrochloride and 9-(3,4-dimethoxy-benzyl)-2,3-dimethoxy-6,7,8,9-tetrahydro-5-thia-8-aza benzocycloheptene-5,5-dioxide.
LC-MS: rt=3.81 min, 581 (M+1, ES+).

EXAMPLE 8

2-[9-(3,4-Dimethoxy-benzyl)-2,3-dimethoxy-5,5-dioxo-5,6,7,9-tetrahydro-5λ$^6$-thia-8-aza-benzocyclohepten-8-yl]-N-indan-1-yl-acetamide prepared by reaction of 2-bromoacetyl bromide with rac-1-aminoindane and 9-(3,4-dimethoxy-benzyl)-2,3-dimethoxy-6,7,8,9-tetrahydro-5-thia-8-aza-benzocycloheptene-5,5-dioxide
LC-MS: rt=4.49 min, 581 (M+1, ES+).

EXAMPLE 9

2-[1-(3,4-Dimethoxy-benzyl)-7,8-dimethoxy-1,3,4,5-tetrahydro-benzo[c]azepin-2-yl]-N-indan-1-yl-acetamide prepared by reaction of 2-bromoacetyl bromide with S(+)-1-aminoindane and 1-(3,4-dimethoxy-benzyl)-7,8-dimethoxy-2,3,4,5-tetrahydro-1H-benzo[c]azepine.
LC-MS: rt=3.80 min, 531 (M+1, ES+).

EXAMPLE 10

2-[5-(3,4-Dimethoxy-benzyl)-7,8-dimethoxy-2,3-dihydro-5H-benzo[f][1,4]oxazepin-4-yl]-N-naphthalen-1-ylmethyl-acetamide prepared by reaction of 2-bromoacetyl bromide with 1-naphtalenemethylamine and 5-(3,4-dimethoxy-benzyl)-7,8-dimethoxy-2,3,4,5-tetrahydro-benzo[f][1,4]oxazepine.
LC-MS: rt=4.39 min, 557 (M+1, ES+).

EXAMPLE 11

2-[5-(3,4-Dimethoxy-benzyl)-7,8-dimethoxy-2,3-dihydro-5H-benzo[f][1,4]oxazepin-4-yl]-N-(2-ethoxy-benzyl)-acetamide prepared by reaction of 2-bromoacetyl bromide with 2-ethoxy-benzylamine and 5-(3,4-dimethoxy-benzyl)-7,8-dimethoxy-2,3,4,5-tetrahydro-benzo[f][1,4]oxazepine
LC-MS: rt=4.34 min, 551 (M+1, ES+).

EXAMPLE 12

2-[5-(3,4-Dimethoxy-benzyl)7,8-dimethoxy-2,3-dihydro-5H-benzo[f][1,4]oxazepin-4-yl]-N-indan-1-yl-acetamide prepared by reaction of 2-bromoacetyl bromide with S(+)-1-aminoindane and 5-(3,4-dimethoxy-benzyl)-7,8-dimethoxy-2,3,4,5-tetrahydro-benzo[f][1,4]oxazepine.
LC-MS: rt=4.32 min, 533 (M+1, ES+).

EXAMPLE 13

2-[9-(3,4-Dimethoxy-benzyl)-2,3-dimethoxy-6,7-dihydro-9H-5-thia-8-aza-benzocyclohepten-8-yl]-N-(1,2,3,4-tetrahydro-naphthalen-1-yl)-acetamide prepared by reaction of 2-bromoacetyl bromide with rac-1,2,3,4-tetrahydro-naphthalen-1-ylamine and 9-(3,4-dimethoxy-benzyl)-2,3-dimethoxy-6,7,8,9-tetrahydro-5-thia-8-aza-benzocycloheptene.
LC-MS: rt=5.01 min, 563 (M+1, ES+).

EXAMPLE 14

N-Benzyl-2-[5-(3,4-dimethoxy-benzyl)-7,8-dimethoxy-2,3-dihydro-5H-benzo[f][1,4]oxazepin-4-yl]-acetamide prepared by reaction of 2-bromoacetyl bromide with benzylamine and 5-(3,4-dimethoxy-benzyl)-7,8-dimethoxy-2,3,4,5-tetrahydro-benzo[f][1,4]oxazepine.
LC-MS: rt=4.05 min, 507 (M+1, ES+).

EXAMPLE 15

2-[9-(3,4-Dimethoxy-benzyl)-2,3-dimethoxy-6,7-dihydro-9H-5-thia-8-aza-benzocyclohepten-8-yl]-N-indan-1-yl-acetamide prepared by reaction of 2-bromoacetyl bromide with S(+)-1-aminoindane and 9-(3,4-dimethoxy-benzyl)-2,3-dimethoxy-6,7,8,9-tetrahydro-5-thia-8-aza-benzocycloheptene.
LC-MS: rt=4.85 min, 549 (M+1, ES+).

EXAMPLE 16

2-[1-(3,4-Dimethoxy-benzyl)-7,8-dimethoxy-1,3,4,5-tetrahydro-benzo[c]azepin-2-yl]-N-(4-methoxy-indan-1-yl)-acetamide prepared by reaction of 2-bromoacetyl bromide with rac-4-methoxy-indan-1-ylamine and 1-(3,4-dimethoxy-benzyl)-7,8-dimethoxy-2,3,4,5-tetrahydro-1H-benzo[c]azepine.
LC-MS: rt=3.83 min, 561 (M+1, ES+).

EXAMPLE 17

2-[1-(3,4-Dimethoxy-benzyl)-7,8-dimethoxy-1,3,4,5-tetrahydro-benzo[c]azepin-2-yl]-N-(3-phenyl-indan-1-yl)-acetamide prepared by reaction of 2-bromoacetyl bromide with rac-3-phenyl-indan-1-ylamine and 1-(3,4-dimethoxy-benzyl)-7,8-dimethoxy-2,3,4,5-tetrahydro-1H-benzo[c]azepine.
LC-MS: rt=4.42 min, 607 (M+1, ES+).

EXAMPLE 18

2-[1-(3,4-Dimethoxy-benzyl)-7,8-dimethoxy-1,3,4,5-tetrahydro-benzo[c]azepin-2-yl]-N-(4-methyl-indan-1-yl)-acetamide prepared by reaction of 2-bromoacetyl bromide with rac-4-methyl-indan-1-ylamine and 1-(3,4-dimethoxy-benzyl)-7,8-dimethoxy-2,3,4,5-tetrahydro-1H-benzo[c]azepine.
LC-MS: rt=4.02 min, 545(M+1, ES+).

EXAMPLE 19

2-[8-Benzyloxy-1-(3,4-dimethoxy-benzyl)-7-methoxy-1,3,4,5-tetrahydro-benzo[c]azepin-2-yl]-N-indan-1-yl-acetamide prepared by reaction of 2-bromoacetyl bromide with S(+)-1-aminoindane and 1-(3,4-dimethoxy-benzyl)-7,8-dimethoxy-2,3,4,5-tetrahydro-1H-benzo[c]azepine.

LC-MS: rt=4.39 min, 607 (M+1, ES+).

C. General Procedure B

To a solution of the respective [1,3,4,5-tetrahydro-benzo[c]azepin-2-yl]-phenyl-acetic acid (1 equivalent) in anhydrous DMF (0.04 M) was added successively PyBOP (1.1 equivalents), the respective amine (1 equivalent) and N,N-diisopropylethylamine (2.3 equivalents). The resulting mixture was stirred at RT for 15 h under nitrogen. Upon completion of the reaction, AcOEt was added, and the organic phase was washed with brine, dried over anhydrous MgSO$_4$, filtered and concentrated in vacuo. Flash chromatography provided the corresponding benzazepine derivative.

EXAMPLE 20

2-[1-(3,4-Dimethoxy-benzyl)-7,8-dimethoxy-1,3,4,5-tetrahydro-benzo[c]azepin-2-yl]-N-indan-2-yl-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 2-aminoindane hydrochloride.

LC-MS: rt=4.26 min, 607 (M+1, ES+).

EXAMPLE 21

N-Butyl-2-[1-(3,4-dimethoxy-benzyl)-7,8-dimethoxy-1,3,4,5-tetrahydro-benzo[c]azepin-2-yl]-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with n-butylamine.

LC-MS: rt=3.91 min, 547 (M+1, ES+).

EXAMPLE 22

2-[1-(3,4-Dimethoxy-benzyl)-7,8-dimethoxy-1,3,4,5-tetrahydro-benzo[c]azepin-2-yl]-N-indan-1-yl-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with S(+)-1-aminoindane.

LC-MS: rt=4.09 min and rt=4.39 min (diastereoisomers), 607 (M+1, ES+).

EXAMPLE 23

N-Benzo[1,3]dioxol-5-ylmethyl-2-[1-(3,4-dimethoxy-benzyl)-7,8-dimethoxy-1,3,4,5-tetrahydro-benzo[c]azepin-2-yl]-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with piperonylamine.

LC-MS: rt=3.88 min and rt=3.98 min (diastereoisomers), 625 (M+1, ES+).

EXAMPLE 24

N-Cyclopentyl-2-[1-(3,4dimethoxy-benzyl)-7,8-dimethoxy-1,3,4,5-tetrahydro-benzo[c]azepin-2-yl]-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with cyclopentylamine.

LC-MS: rt=3.79 min and rt=3.92 min (diastereoisomers), 559 (M+1, ES+).

EXAMPLE 25

2-[1-(3,4-Dimethoxy-benzyl)-7,8-dimethoxy-1,3,4,5-tetrahydro-benzo[c]azepin-2-yl]-N-furan-2-ylmethyl-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with furfurylamine.

LC-MS: rt=3.72 min and rt=3.85 min (diastereoisomers), 571 (M+1, ES+).

EXAMPLE 26

{2-[1-(3,4-Dimethoxy-benzyl)-7,8-dimethoxy-1,3,4,5-tetrahydro-benzo[c]azepin-2-yl]-2-phenyl-acetylamino}-acetic acid ethyl ester prepared by reaction of [1-(3,4-dimethoxy-benzyl)-7,8-dimethoxy-1,3,4,5-tetrahydro-benzo[c]azepin-2-yl]-phenyl-acetic acid with glycine ethyl ester hydrochloride.

LC-MS: rt=3.72 min, 577 (M+1, ES+).

EXAMPLE 27

2-[1-(3,4-Dimethoxy-benzyl)-7,8-dimethoxy-1,3,4,5-tetrahydro-benzo[c]azepin-2-yl]-2-phenyl-N-pyridin-4-ylmethyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 4-picolylamine.

LC-MS: rt=3.09 min, 582 (M+1, ES+).

EXAMPLE 28

2-[1-(3,4-Dimethoxy-benzyl)-7,8-dimethoxy-1,3,4,5-tetrahydro-benzo[c]azepin-2-yl]-2-phenyl-N-pyridin-3-ylmethyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 3-picolylamine.

LC-MS: rt=3.20 min, 582 (M+1, ES+).

EXAMPLE 29

N-Cyclopropyl-2-[1-(3,4-dimethoxy-benzyl)-7,8-dimethoxy-1,3,4,5-tetrahydro-benzo[c]azepin-2-yl]-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with cyclopropylamine.
LC-MS: rt=3.59 min, 531 (M+1, ES+).

EXAMPLE 30

2-[1-(3,4-Dimethoxy-benzyl)-7.8-dimethoxy-1,3,4,5-tetrahydro-benzo[c]azepin-2-yl]-N-(2-oxo-tetrahydro-furan-3-yl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 2-amino-4-butyrolactone hydrobromide.
LC-MS: rt=3.46 min, 575 (M+1, ES+).

EXAMPLE 31

2-{2-[1-(3,4-Dimethoxy-benzyl)-7,8-dimethoxy-1,3,4,5-tetrahydro-benzo[c]azepin-2-yl]-2-phenyl-acetylamino}-3-hydroxy-propionic acid methyl ester prepared by reaction of [1-(3,4-dimethoxy-benzyl)-7,8-dimethoxy-1,3,4,5-tetrahydro-benzo[c]azepin-2-yl]-phenyl-acetic acid with L-serine methyl ester hydrochloride.
LC-MS: rt=3.40 min, 593 (M+1, ES+).

EXAMPLE 32

2-[1-(3,4-Dimethoxy-benzyl)-7,8-dimethoxy-1,3,4,5-tetrahydro-benzo[c]azepin-2-yl]-N-ethylcarbamoylmethyl-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 2-amino-N-ethyl-acetamide.
LC-MS: rt=3.37 min, 576 (M+1, ES+).

EXAMPLE 33

2-[1-(3,4-Dimethoxy-benzyl)-7,8-dimethoxy-1,3,4,5-tetrahydro-benzo[c]azepin-2-yl]-N-[(ethyl-methyl-carbamoyl)-methyl]-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 2-amino-N-ethyl-N-methyl-acetamide.
LC-MS: rt=3.42 min, 590 (M+1, ES+).

EXAMPLE 34

3-{2-[1-(3,4-Dimethoxy-benzyl)-7,8-dimethoxy-1,3,4,5-tetrahydro-benzo[c]azepin-2-yl]-2-phenyl-acetylamino}-propionic acid methyl ester prepared by reaction of [1-(3,4-dimethoxy-benzyl)-7,8-dimethoxy-1,3,4,5-tetrahydro-benzo[c]azepin-2-yl]-phenyl-acetic acid with 3-amino-propionic acid methyl ester.
LC-MS: rt=3.52 min, 577 (M+1, ES+).

EXAMPLE 35

N-(1H-Benzoimidazol-2-ylmethyl)-2-[1-(3,4-dimethoxy-benzyl)-7,8-dimethoxy-1,3,4,5-tetrahydro-benzo[c]azepin-2-yl]-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 2-aminomethyl-benzimidazole dihydrochloride hydrate.
LC-MS: rt=3.36 min, 621 (M+1, ES+).

EXAMPLE 36

3-{2-[1-(3,4-Dimethoxy-benzyl)-7,8-dimethoxy-1,3,4,5-tetrahydro-benzo[c]azepin-2-yl]-2-phenyl-acetylamino}-N,N-dimethyl-propionamide prepared by reaction of [1-(3,4-dimethoxy-benzyl)-7,8-dimethoxy-1,3,4,5-tetrahydro-benzo[c]azepin-2-yl]-phenyl-acetic acid with 3-amino-N,N-dimethyl-propionamide.
LC-MS: rt=3.42 min, 590 (M+1, ES+).

EXAMPLE 37

3-{2-[1-(3,4-Dimethoxy-benzyl)-7,8-dimethoxy-1,3,4,5-tetrahydro-benzo[c]azepin-2-yl]-2-phenyl-acetylamino}-N-ethyl-N-methyl-propionamide prepared by reaction of [1-(3,4-dimethoxy-benzyl)-7,8-dimethoxy-1,3,4,5-tetrahydro-benzo[c]azepin-2-yl]-phenyl-acetic acid with 3-amino-N-ethyl-N-methyl-propionamide.
LC-MS: rt=3.40 min, 604 (M+1, ES+).

EXAMPLE 38

2-[1-(3,4-Dimethoxy-benzyl)-7,8-dimethoxy-1,3,4,5-tetrahydro-benzo[c]azepin-2-yl]-N-(1-methyl-1H-indol-3-ylmethyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with C-(1-methyl-1H-indol-3-yl)-methylamine.
LC-MS: rt=3.99 min and rt=4.12 min (diastereoisomers), 634 (M+1, ES+).

EXAMPLE 39

2-[1-(3,4-Dimethoxy-benzyl)-7,8-dimethoxy-1,3,4,5-tetrahydro-benzo[c]azepin-2-yl]-N-isoxazol-5-ylmethyl-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with C-isoxazol-5-yl-methylamine hydrochloride.
LC-MS: rt=3.65 min, 572 (M+1, ES+).

EXAMPLE 40

2-[1-(3,4-Dimethoxy-benzyl)-7,8-dimethoxy-1,3,4,5-tetrahydro-benzo[c]azepin-2-yl]-N-(1H-indol-3-ylmethyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with C-(1H-indol-3-yl)-methylamine dihydrochloride.

LC-MS: rt=3.82 mm and rt=3.96 min (diastereoisomers), 620 (M+1, ES+).

EXAMPLE 41

2-[1-(3,4-Dimethoxy-benzyl)-7,8-dimethoxy-1,3,4,5-tetrahydro-benzo[c]azepin-2-yl]-N-(1-methyl-1H-benzoimidazol-2-ylmethyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with C-(1-methyl-1H-benzoimidazol-2-yl)-methylamine.

LC-MS: rt=3.50 min, 635 (M+1, ES+).

EXAMPLE 42

2-[1-(3,4-Dimethoxy-benzyl)-7,8-dimethoxy-1,3,4,5-tetrahydro-benzo[c]azepin-2-yl]-N-isoquinolin-1-ylmethyl-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with C-isoquinolin-1-yl-methylamine dihydrochloride.

LC-MS: rt=3.88 min, 632 (M+1, ES+).

EXAMPLE 43

2-[1-(3,4-Dimethoxy-benzyl)-7,8-dimethoxy-1,3,4,5-tetrahydro-benzo[c]azepin-2-yl]-2-phenyl-N-(4-[1,2,3]thiadiazol-4-yl-benzyl)-acetamide prepared by reaction of [1-(3,4-dimethoxy-benzyl)-7,8-dimethoxy-1,3,4,5-tetrahydro-benzo[c]azepin-2-yl]-phenyl-acetic acid with 4-(1,2,3-thiadiazol-4-yl)benzylamine hydrochloride.

LC-MS: rt=4.09 min, 665 (M+1, ES+).

EXAMPLE 44

2-[1-(3,4-Dimethoxy-benzyl)-7,8-dimethoxy-1,3,4,5-tetrahydro-benzo[c]azepin-2-yl]-N-(1-methyl-1H-indazol-3-ylmethyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with C-(1-methyl-1H-indazol-3-yl)-methylamine hydrochloride.

LC-MS: rt=3.83 min, 635 (M+1, ES+).

EXAMPLE 45

N-Cyanomethyl-2-[1-(3,4-dimethoxy-benzyl)-7,8-dimethoxy-1,3,4,5-tetrahydro-benzo[c]azepin-2-yl]-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with amino acetonitrile hydrochloride.

LC-MS: rt=3.42 min and rt=3.58 min (diastereoisomers), 530 (M+1, ES+).

EXAMPLE 46

N-(2-Acetylamino-ethyl)-2-[1-(3,4-dimethoxy-benzyl)-7,8-dimethoxy-1,3,4,5-tetrahydro-benzo[c]azepin-2-yl]-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with N-acetylethylendiamine.

LC-MS: rt=3.13 min, 576 (M+1, ES+).

EXAMPLE 47

2-[1-(3,4-Dimethoxy-benzyl)-7,8-dimethoxy-1,3,4,5-tetrahydro-benzo[c]azepin-2-yl]-2-phenyl-N-(2,2,2-trifluoro-ethyl)-acetamide prepared by reaction of [1-(3,4-dimethoxy-benzyl)-7,8-dimethoxy-1,3,4,5-tetrahydro-benzo[c]azepin-2-yl]-phenyl-acetic acid with 2,2,2-trifluoroethylamine.

LC-MS: rt=4.11 min, 573 (M+1, ES+).

EXAMPLE 48

2-[1-(3,4-Dimethoxy-benzyl)-7,8-dimethoxy-1,3,4,5-tetrahydro-benzo[c]azepin-2-yl]-N-(2-methylsulfanyl-ethyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 2-(methylthio)-ethylamine.

LC-MS: rt=3.63 min, 565 (M+1, ES+).

EXAMPLE 49

2-[1-(3,4-Dimethoxy-benzyl)-7,8-dimethoxy-1,3,4,5-tetrahydro-benzo[c]azepin-2-yl]-2-phenyl-N-quinolin-2-ylmethyl-acetamide prepared by reaction of [1-(3,4-dimethoxy-benzyl)-7,8-dimethoxy-1,3,4,5-tetrahydro-benzo[c]azepin-2-yl]-phenyl-acetic acid with C-quinolin-2-yl-methylamine dihydrochloride.

LC-MS: rt=3.91 min, 632 (M+1, ES+).

EXAMPLE 50

N-(2-Cyano-ethyl)-2-[1-(3,4-dimethoxy-benzyl)-7,8-dimethoxy-1,3,4,5-tetrahydro-benzo[c]azepin-2-yl]-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 3-aminopropionitrile.

LC-MS: rt=3.30 min, 544 (M+1, ES+).

EXAMPLE 51

2-[1-(3,4-Dimethoxy-benzyl)-7,8-dimethoxy-1,3,4,5-tetrahydro-benzo[c]azepin-2-yl]-N-(3-methoxy-propyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 3-methoxypropylamine.

LC-MS: rt=3.32 min, 563 (M+1, ES+).

EXAMPLE 52

2-[1-(3,4-Dimethoxy-benzyl)-7,8-dimethoxy-1,3,4,
5-tetrahydro-benzo[c]azepin-2-yl]-N-(3-ethoxy-propyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 3-ethoxypropylamine.
LC-MS: rt=3.51 min, 577 (M+1, ES+).

EXAMPLE 53

2-[1-(3,4-Dimethoxy-benzyl)-7,8-dimethoxy-1,3,4,
5-tetrahydro-benzo[c]azepin-2-yl]-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with ammonium chloride.
LC-MS: rt=3.15 min, 491 (M+1, ES+).

EXAMPLE 54

2-[1-(3,4-Dimethoxy-benzyl)-7,8-dimethoxy-1,3,4,
5-tetrahydro-benzo[c]azepin-2-yl]-2-phenyl-N-pyrazin-2-ylmethyl-acetamide prepared by reaction of [1-(3,4-dimethoxy-benzyl)-7,8-dimethoxy-1,3,4,5-tetrahydro-benzo[c]azepin-2-yl]-phenyl-acetic acid with C-pyrazin-2-yl-methylamine hydrochloride.
LC-MS: rt=3.33 min, 583 (M+1, ES+).

EXAMPLE 55

2-[1-(3,4-Dimethoxy-benzyl)-7,8-dimethoxy-1,3,4,
5-tetrahydro-benzo[c]azepin-2-yl]-2-phenyl-N-prop-2-ynyl-acetamide prepared by reaction of [1-(3,4-dimethoxy-benzyl)-7,8-dimethoxy-1,3,4,5-tetrahydro-benzo[c]azepin-2-yl]-phenyl-acetic acid with propargylamine.
LC-MS: rt=3.36 min and rt=3.51 min (diastereoisomers), 529 (M+1, ES+).

EXAMPLE 56

N-tert-Butyl-2-[1-(3,4-dimethoxy-benzyl)-7,8-dimethoxy-1,3,4,5-tetrahydro-benzo[c]azepin-2-yl]-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with tert-butylamine.
LC-MS: rt=3.69 min, 547 (M+1, ES+).

EXAMPLE 57

2-[1-(3,4-Dimethoxy-benzyl)-7,8-dimethoxy-1,3,4,
5-tetrahydro-benzo[c]azepin-2-yl]-N-(3-methyl-butyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 1-amino-3-methylbutane.
LC-MS: rt=3.89 min, 561 (M+1, ES+).

EXAMPLE 58

2-[1-(3,4-Dimethoxy-benzyl)-7,8-dimethoxy-1,3,4,
5-tetrahydro-benzo[c]azepin-2-yl]-N-(3,3-dimethyl-butyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 3,3-dimethylbutylamine.
LC-MS: rt=4.20 min, 575 (M+1, ES+).

EXAMPLE 59

2-[1-(3,4-Dimethoxy-benzyl)-7,8-dimethoxy-1,3,4,
5-tetrahydro-benzo[c]azepin-2-yl]-N-(1-ethyl-propyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 1-ethylpropylamine.
LC-MS: rt=3.77 min, 561 (M+1, ES+).

EXAMPLE 60

2-[1-(3,4-Dimethoxy-benzyl)-7,8-dimethoxy-1,3,4,
5-tetrahydro-benzo[c]azepin-2-yl]-N-(2-ethylsulfanyl-ethyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 2-(ethylthio)ethylamine hydrochloride.
LC-MS: rt=3.72 min, 579 (M+1, ES+).

EXAMPLE 61

2-[1-(3,4-Dimethoxy-benzyl)-7,8-dimethoxy-1,3,4,
5-tetrahydro-benzo[c]azepin-2-yl]-N-(2-hydroxy-ethyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with ethanolamine.
LC-MS: rt=3.19 min, 535 (M+1, ES+).

EXAMPLE 62

2-[1-(3,4-Dimethoxy-benzyl)-7,8-dimethoxy-1,3,4,
5-tetrahydro-benzo[c]azepin-2-yl]-N-(3-hydroxy-propyl)-2-phenyl-acetamide prepared by reaction of [1-(3,4-dimethoxy-benzyl)-7,8-dimethoxy-1,3,4,5-tetrahydro-benzo[c]azepin-2-yl]-phenyl-acetic acid with 3-amino-1-propanol.
LC-MS: rt=3.13 min, 549 (M+1, ES+).

EXAMPLE 63

[1-(3,4-Dimethoxy-benzyl)-7,8-dimethoxy-1,3,4,5-tetrahydro-benzo[c]azepin-2-yl]-phenyl-acetic acid N',N'-dimethyl-hydrazide prepared by reaction of [1-(3,4-dimethoxy-benzyl)-7,8-dimethoxy-1,3,4,5-tetrahydro-benzo[c]azepin-2-yl]-phenyl-acetic acid with N,N-dimethylhydrazine.
LC-MS: rt=3.20 min, 534 (M+1, ES+).

D. Variation of Substituents on Position 8:

General Procedure:

To a solution of the respective 8-benzyloxy-1,3,4,5-tetrahydro-benzazepine in methanol (0.07 M) was added palladium (10 wt. % on activated charcoal; 10% of the benzylether weight) and the resulting heterogeneous mixture was vigorously stirred under an hydrogen atmosphere at RT until disappearance of benzylether (TLC). Upon complete conversion the mixture was filtered through celite and concentrated in vacuo. Flash chromatography yielded the pure phenol derivative. To a solution of this phenol derivative (1 equivalent) in anhydrous DMF (0.04 M) was added successively anhydrous potassium carbonate (5 equivalents) and the respective electrophile (1.2 equivalents). The resulting heterogeneous mixture was stirred at 50° C. for up to 15 h. After reaction the mixture was dissolved in AcOEt and washed with a saturated aqueous solution of NaHCO$_3$. The organic phase was dried over anhydrous MgSO$_4$, filtered and concentrated in vacuo. Flash chromatography provided the pure benzazepine derivative.

EXAMPLE 64

2-[1-(3,4-Dimethoxy-benzyl)-8-hydroxy-7-methoxy-1,3,4,5-tetrahydro-benzo[c]azepin-2-yl]-N-indan-1-yl-acetamide prepared by hydrogenolysis of 2-[8-benzyloxy-1-(3,4-dimethoxy-benzyl)-7-methoxy-1,3,4,5-tetrahydro-benzo[c]azepin-2-yl]-N-indan-1-yl-acetamide.
LC-MS: rt=3.64 min, 517 (M+1, ES+).

EXAMPLE 65

N-Benzo[1,3]dioxol-5-ylmethyl-2-[1-(3,4-dimethoxy-benzyl)-8-hydroxy-7-methoxy-1,3,4,5-tetrahydro-benzo[c]azepin-2-yl]-2-phenyl-acetamide prepared by hydrogenolysis of N-benzo[1,3]dioxol-5-ylmethyl-2-[8-benzyloxy-1-(3,4-dimethoxy-benzyl)-7-methoxy-1,3,4,5-tetrahydro-benzo[c]azepin-2-yl]-2-phenyl-acetamide.
LC-MS: rt=3.77 min, 611 (M+1, ES+).

EXAMPLE 66

2-[8-Allyloxy-1-(3,4-dimethoxy-benzyl)-7-methoxy-1,3,4,5-tetrahydro-benzo[c]azepin-2-yl]-N-indan-1-yl-acetamide prepared by reaction of 2-[1-(3,4-dimethoxy-benzyl)-8-hydroxy-7-methoxy-1,3,4,5-tetrahydro-benzo[c]azepin-2-yl]-N-indan-1-yl-acetamide with allylbromide.
LC-MS: rt=4.05 min, 557 (M+1, ES+).

EXAMPLE 67

2-[1-(3,4-Dimethoxy-benzyl)-7-methoxy-8-propoxy-1,3,4,5-tetrahydro-benzo[c]azepin-2-yl]-N-indan-1-yl-acetamide prepared by reaction of 2-[1-(3,4-dimethoxy-benzyl)-8-hydroxy-7-methoxy-1,3,4,5-tetrahydro-benzo[c]azepin-2-yl]-N-indan-1-yl-acetamide with 1-bromopropane.
LC-MS: rt=4.13 min, 559 (M+1, ES+).

EXAMPLE 68

2-[1-(3,4-Dimethoxy-benzyl)-8-isopropoxy-7-methoxy-1,3,4,5-tetrahydro-benzo[c]azepin-2-yl]-N-indan-1-yl-acetamide prepared by reaction of 2-[1-(3,4-dimethoxy-benzyl)-8-hydroxy-7-methoxy-1,3,4,5-tetrahydro-benzo[c]azepin-2-yl]-N-indan-1-yl-acetamide with 2-bromopropane.
LC-MS: rt=4.07 min, 559 (M+1, ES+).

EXAMPLE 69

2-[8-(2,2-Difluoro-ethoxy)-1-(3,4-dimethoxy-benzyl)-7-methoxy-1,3,4,5-tetrahydro-benzo[c]azepin-2-yl]-N-indan-1-yl-acetamide prepared by reaction of 2-[1-(3,4-dimethoxy-benzyl)-8-hydroxy-7-methoxy-1,3,4,5-tetrahydro-benzo[c]azepin-2-yl]-N-indan-1-yl-acetamide with 2-bromo-1,1-difluoroethane.
LC-MS: rt=4.14 min, 581 (M+1, ES+).

EXAMPLE 70

N-Benzo[1,3]dioxol-5-ylmethyl-2-[8-(2,2-difluoro-ethoxy)-1-(3,4-dimethoxy-benzyl)-7-methoxy-1,3,4,5-tetrahydro-benzo[c]azepin-2-yl]-2-phenyl-acetamide prepared by reaction of N-benzo[1,3]dioxol-5-ylmethyl-2-[1-(3,4-dimethoxy-benzyl)-8-hydroxy-7-methoxy-1,3,4,5-tetrahydro-benzo[c]azepin-2-yl]-2-phenyl-acetamide with 2-bromo-1,1-difluoroethane.
LC-MS: rt=4.20 min and rt=4.37 min (diastereoisomers), 675 (M+1, ES+).

EXAMPLE 71

N-Benzo[1,3]dioxol-5-ylmethyl-2-[1-(3,4-dimethoxy-benzyl)-8-isopropoxy-7-methoxy-1,3,4,5-tetrahydro-benzo[c]azepin-2-yl]-2-phenyl-acetamide prepared by reaction of N-benzo[1,3]dioxol-5-ylmethyl-2-[1-(3,4-dimethoxy-benzyl)-8-hydroxy-7-methoxy-1,3,4,5-tetrahydro-benzo[c]azepin-2-yl]-2-phenyl-acetamide with 2-bromopropane.
LC-MS: rt=3.96 min, 653 (M+1, ES+).

E. 1,4-Benzodiazepin-2-ones:

EXAMPLE 72

2-[5-(3,4-Dichloro-benzyl)-7,8-dimethoxy-2-oxo-1,2,3,5-tetrahydro benzo[e][1,4]diazepin-4-yl]-N-indan-1-yl-acetamide prepared according to general procedure A, by reaction of 2-bromoacetyl bromide with S(+)-1-aminoindane and 5-(3,4-dichloro-benzyl)-7,8-dimethoxy-1,3,4,5-tetrahydro-benzo[e][1,4]diazepin-2-one.
LC-MS: rt=5.18 min, 554.47 (M+1, ES+).

F. Optically Pure Benzazepines:

The preparation of enantiomerically pure 1-substituted-2-tetrahydrobenzazepine derivatives was based on the methodology described by Polniaszek, in the case of optically pure 1-substituted tetrahydroisoquinolines (Polniaszek R. P. et al., *J. Am. Chem. Soc.* 1989, 111, 4859–4863). For the Bischler-Napieralski reaction, the experimental conditions described by Kano were employed (S. Kano et al., *Chem. Pharm. Bull.* 1977, 25, 10, 2510–2515).

1-(S)-(3,4-dimethoxy-benzyl)-7,8-dimethoxy-2,3,4,5-tetrahydro-1H benzo[c]azepine 2-(3,4-Dimethoxy-phenyl)-N-[3-(3,4-dimethoxy-phenyl)-propyl]-N-(1-(S)-phenyl-ethyl)-acetamide was prepared according to the described procedures (Polniaszek R. P. et al., *J. Am. Chem. Soc.* 1989, 111, 4859–4863).

A mixture of 2-(3,4-dimethoxy-phenyl)-N-[3-(3,4-dimethoxy-phenyl)-propyl]-N-(1-(S)-phenyl-ethyl)-acetamide (7.0 g, 14.65 mmol) and phosphorus oxide chloride (13.4 ml, 146.5 mmol) in anhydrous acetonitrile, (160 ml) was heated at reflux for 6.5 h, under nitrogen. After cooling to RT, the volatiles were removed under vacuum and the resulting oil was dissolved in anhydrous methanol before evaporation to dryness (repeated twice). The resulting brown oil was dissolved again in anhydrous methanol (122 ml) and cooled at −78° C., under nitrogen. Then, sodium borohydride (3.02 g, 79.99 mmol) was added portionwise in 5 h to the reaction mixture kept at −78° C. The reaction was quenched by dropwise addition of aqueous 1N HCl (8 ml) and the mixture was allowed to warm to RT before the solvent was removed under vacuum and water (175 ml) was added. After extraction with $CH_2Cl_2$ (4×150 ml), the organic layer was dried over anhydrous magnesium sulfate and the solvent was removed under vacuum. The resulting crude oil was purified by flash chromatography ($CH_2Cl_2/CH_3OH$: 36/1) giving the pure diastereoisomer 1-(S)-(3,4-dimethoxy-benzyl)-7,8-dimethoxy-2-(1-(S)-phenyl-ethyl)-2,3,4,5-tetrahydro-1H-benzo[c]azepine as a yellow oil (1.36 g, 20%).

This compound (225 mg, 0.49 mmol) was then dissolved in methanol (8 ml) and 10% palladium on charcoal (225 mg) and trifluoroacetic acid (0.05 ml, 0.65 mmol) were added. The resulting mixture was stirred under hydrogen (1 atm), at RT for 13 h. After filtration over celite and evaporation to dryness, water (10 ml) and aqueous 2N NaOH (0.35 ml, 0.70 mmol) were added. The mixture was extracted with $CH_2Cl_2$ (3×15 ml) and the organic extract was dried over anhydrous $MgSO_4$, filtered and concentrated under vacuum. The optically pure 1-(S)-(3,4-dimethoxy-benzyl)-7,8-dimethoxy-2,3,4,5-tetrahydro-1H-benzo[c]azepine was obtained as a yellow oil (152 mg, 88%).
LC-MS: rt=3.04 min, 358 (M+1, ES+).

EXAMPLE 73

2-[1-(S)-(3,4-Dimethoxy-benzyl)-7,8-dimethoxy-1,3,4,5-tetrahydro-benzo[c]azepin-2-yl]-N-indan-(S)-1-yl-acetamide prepared according to general procedure A, by reaction of 2-bromoacetyl bromide with S(+)-1-aminoindane and 1-(S)-(3,4-dimethoxy-benzyl)-7,8-dimethoxy-2,3,4,5-tetrahydro-1H-benzo[c]azepine.
LC-MS: rt=3.76 min, 531 (M+1, ES+).

EXAMPLE 74

2-[1-(S)-(3,4-Dimethoxy-benzyl)-7,8-dimethoxy-1,3,4,5-tetrahydro-benzo[c]azepin-2-yl]-N-indan-2-yl-acetamide prepared according to general procedure A, by reaction of 2-bromoacetyl bromide with 2-aminoindane hydrochloride and 1-(S)-(3,4-dimethoxy-benzyl)-7,8-dimethoxy-2,3,4,5-tetrahydro-1H-benzo[c]azepine.
LC-MS: rt=3.70 min, 531 (M+1, ES+).

What is claimed is:
1. A compound of formula (I)

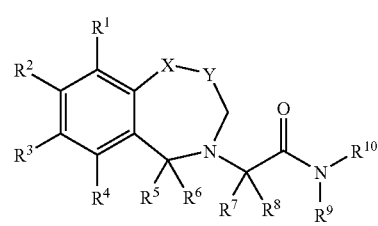

Formula (I)

or an optically pure enantiomer, a mixture of enantiomers, an optically pure diastereoisomer, a mixture of diastereoisomers, a diastereoisomeric racemate, a mixture of diastereoisomeric racemates, a meso form; or a pharmaceutically acceptable salt thereof;
wherein:
$R^1$, $R^2$, $R^3$, $R^4$ independently represent cyano, nitro, halogen, hydrogen, hydroxy, lower alkyl, lower alkenyl, lower alkoxy, lower alkenyloxy, trifluoromethyl, trifluoromethoxy, cycloalkyloxy, aryloxy, aralkyloxy, heterocyclyloxy, heterocyclylalkyloxy, $R^{11}CO—$, $NR^{12}R^{13}CO—$, $R^{12}R^{13}N—$, $R^{11}OOC—$, $R^{11}SO_2NH—$, or $R^{14}—CO—NH—$, or $R^2$ and $R^3$ together as well as $R^1$ and $R^2$ together and $R^3$ and $R^4$ together may form with the phenyl ring a five, six or seven-membered saturated ring comprising one or two oxygen atoms;
$R^5$ represents aryl, aralkyl, lower alkyl, lower alkenyl, trifluoromethyl, cycloalkyl, heterocyclyl or heterocyclyl-lower alkyl;
$R^6$ represents hydrogen, aryl, aralkyl, lower alkyl, lower alkenyl, trifluoromethyl, cycloalkyl, heterocyclyl or heterocyclyl-lower alkyl;
$R^7$, $R^8$ independently represent hydrogen, aryl, aralkyl, lower alkyl, lower alkenyl, cycloalkyl, heterocyclyl or heterocyclyl-lower alkyl;
$R^9$, $R^{10}$ independently represent hydrogen, aryl, arylcycloalkyl, aralkyl, lower alkyl, lower alkenyl, lower alkinyl, cycloalkyl, heterocyclyl or heterocyclyl-lower alkyl, in which one, several, or all hydrogen atoms may be replaced by halogen or in which one or two hydrogen atoms may be replaced by hydroxy, nitro, cyano, trifluoromethyl, trifluoromethoxy, —O-lower alkyl, —NH-lower alkyl, —N(lower alkyl)$_2$, —S-lower alkyl, —COO-lower alkyl, —CONH-lower alkyl, —CON(lower alkyl)$_2$, —CO-lower alkyl, —NHCO-lower alkyl, —O-lower alkenyl with 3 to 5 carbon atoms, —NH-lower alkenyl with 3 to 5 carbon atoms, —N(lower alkenyl with 3 to 5 carbon atoms)$_2$, —S-lower alkenyl with 3 to 5 carbon atoms, —COO-lower alkenyl with 3 to 5 carbon atoms, —CONH-lower alkenyl with 3 to 5 carbon atoms, —CON(lower alkenyl with 3 to 5 carbon atoms)$_2$, —CO-lower alkenyl with 3 to 5 carbon atoms, —NHCO-lower alkenyl with 3 to 5 carbon atoms, —O-lower alkinyl with 3 to 5 carbon atoms, —NH-lower alkinyl with 3 to 5 carbon atoms, —N(lower alkinyl with 3 to 5 carbon atoms)$_2$, —S-lower alkinyl with 3 to 5 carbon atoms, —COO-lower alkinyl with 3 to 5 carbon atoms, —CONH-lower alkinyl with 3 to 5 carbon atoms, —CON(lower alkinyl with 3 to 5 carbon atoms)$_2$, or —NHCO-lower alkinyl with 3 to 5 carbon atoms;

$R^{11}$ represents lower alkyl, aryl, aralkyl, heterocyclyl or heterocyclyl-lower alkyl;

$R^{12}$ and $R^{13}$ independently represent hydrogen, lower alkyl, cycloalkyl, aryl, aralkyl, heterocyclyl or heterocyclyl-lower alkyl;

$R^{14}$ represents lower alkyl, aryl, cycloalkyl, heterocyclyl, $R^{12}R^{13}N$—, $R^{11}O$—; and —X—Y— is —CH$_2$—CH$_2$—.

2. A compounds of the formula (II)

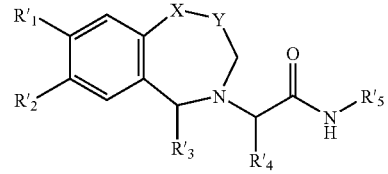

Formula (II)

or an optically pure enantiomer, a mixture of enantiomers, an optically pure diastereoisomer, a mixture of diastereoisomers, a diastereoisomeric racemate, a mixture of diastereoisomeric racemates, a meso form; or a pharmaceutically acceptable salt thereof;

wherein:
$R^1$, $R^2$, $R^3$, $R^4$ independently represent cyano, nitro, halogen, hydrogen, hydroxy, lower alkyl, lower alkenyl, lower alkoxy, lower alkenyloxy, trifluoromethyl, trifluoromethoxy, cycloalkyloxy, aryloxy, aralkyloxy, heterocyclyloxy, heterocyclylalkyloxy, $R^{11}CO$—, $NR^{12}R^{13}CO$—, $R^{12}R^{13}N$—, $R^{11}OOC$—, $R^{11}SO_2NH$—, or $R^{14}$—CO—NH—, or $R^2$ and $R^3$ together as well as $R^1$ and $R^2$ together and $R^3$ and $R^4$ together may form with the phenyl ring a five, six or seven-membered saturated ring comprising one or two oxygen atoms;

$R^5$ independently represents aryl, aralkyl, lower alkyl, lower alkenyl, trifluoromethyl, cycloalkyl, heterocyclyl or heterocyclyl-lower alkyl;

$R^6$ independently represents hydrogen, aryl, aralkyl, lower alkyl, lower alkenyl, trifluoromethyl, cycloalkyl, heterocyclyl or heterocyclyl-lower alkyl;

$R^7$, $R^8$, $R^9$, $R^{10}$ independently represent hydrogen, aryl, aralkyl, lower alkyl, lower alkenyl, cycloalkyl, heterocyclyl or heterocyclyl-lower alkyl;

$R^{11}$ represents lower alkyl, aryl, aralkyl, heterocyclyl or heterocyclyl-lower alkyl;

$R^{12}$ and $R^{13}$ independently represent hydrogen, lower alkyl, cycloalkyl, aryl, aralkyl, heterocyclyl or heterocyclyl-lower alkyl;

$R^{14}$ represents lower alkyl, aryl, cycloalkyl, heterocyclyl, $R^{12}R^{13}N$—, $R^{11}O$—; and —X—Y— is —CH$_2$—CH$_2$—.

3. A compounds of the formula (III)

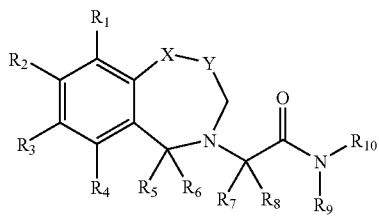

Formula (III)

or an optically pure enantiomer, a mixture of enantiomers, an optically pure diastereoisomer, a mixtures of diastereoisomers, a diastereoisomeric racemate, a mixture of diastereoisomeric racemates, a meso form; or a pharmaceutically acceptable salt thereof;

wherein:
$R'^1$ and $R'^2$ independently represent hydrogen, hydroxy, lower alkoxy, lower alkenyloxy or halogen or may form with the phenyl ring a five, six or seven membered-ring comprising one or two oxygen atoms;

$R'^3$ represents aryl, aralkyl, lower alkyl, lower alkenyl, cycloalkyl, heterocyclyl or heterocyclyl-lower alkyl;

$R'^4$, $R'^5$ independently represent hydrogen, aryl, aralkyl, lower alkyl, lower alkenyl, cycloalkyl, heterocyclyl or heterocyclyl-lower alkyl; and —X—Y— is —CH$_2$—CH$_2$.

4. The compound according to claim 1, selected from the group consisting of:

2-[1-(3,4-Dimethoxy-benzyl)-7,8-dimethoxy-1,3,4,5-tetrahydro-benzo[c]azepin-2-yl]-N-naphthalen-1-ylmethyl-acetamide;

2-[1-(3,4-Dimethoxy-benzyl)-7,8-dimethoxy-1,3,4,5-tetrahydro-benzo[c]azepin-2-yl]-N-indan-2-yl-acetamide;

2-[1-(3,4-Dimethoxy-benzyl)-7,8-dimethoxy-1,3,4,5-tetrahydro-benzo[c]azepin-2-yl]-N-indan-1-yl-acetamide;

2-[1-(3,4-Dimethoxy-benzyl)-7,8-dimethoxy-1,3,4,5-tetrahydro-benzo[c]azepin-2-yl]-N-indan-2-yl-2-phenyl-acetamide;

N-Butyl-2-[1-(3,4-dimethoxy-benzyl)-7,8-dimethoxy-1,3,4,5-tetrahydro-benzo[c]azepin-2-yl]-2-phenyl-acetamide;

2-[1-(3,4-Dimethoxy-benzyl)-7,8-dimethoxy-1,3,4,5-tetrahydro-benzo[c]azepin-2-yl]-N-indan-1-yl-2-phenyl-acetamide;

N-Cyclopentyl-2-[1-(3,4-dimethoxy-benzyl)-7,8-dimethoxy-1,3,4,5-tetrahydro-benzo[c]azepin-2-yl]-2-phenyl-acetamide;

2-[1-(3,4-Dimethoxy-benzyl)-7,8-dimethoxy-1,3,4,5-tetrahydro-benzo[c]azepin-2-yl]-N-furan-2-ylmethyl-2-phenyl-acetamide;

{2-[1-(3,4-Dimethoxy-benzyl)-7,8-dimethoxy-1,3,4,5-tetrahydro-benzo[c]azepin-2-yl]-2-phenyl-acetylamino}-acetic acid ethyl ester;

2-[1-(3,4-Dimethoxy-benzyl)-7,8-dimethoxy-1,3,4,5-tetrahydro-benzo[c]azepin-2-yl]-2-phenyl-N-pyridin-4-ylmethyl-acetamide 2-[1-(3,4-Dimethoxy-benzyl)-7,8-dimethoxy-1,3,4,5-tetrahydro-benzo[c]azepin-2-yl]-2-phenyl-N-pyridin-3-ylmethyl-acetamide;

N-Cyclopropyl-2-[1-(3,4-dimethoxy-benzyl)-7,8-dimethoxy-1,3,4,5-tetrahydro-benzo[c]azepin-2-yl]-2-phenyl-acetamide;

2-[1-(3,4-Dimethoxy-benzyl)-7,8-dimethoxy-1,3,4,5-tetrahydro-benzo[c]azepin-2-yl]-N-(4-methoxy-indan-1-yl)-acetamide;

2-{2-[1-(3,4-Dimethoxy-benzyl)-7,8-dimethoxy-1,3,4,5-tetrahydro-benzo[c]azepin-2-yl]-2-phenyl-acetylamino}-3-hydroxy-propionic acid methyl ester;

2-[1-(3,4-Dimethoxy-benzyl)-7,8-dimethoxy-1,3,4,5-tetrahydro-benzo[c]azepin-2-yl]-N-ethylcarbamoylmethyl-2-phenyl-acetamide;

2-[1-(3,4-Dimethoxy-benzyl)-7,8-dimethoxy-1,3,4,5-tetrahydro-benzo[c]azepin-2-yl]-N-[(ethyl-methyl-carbamoyl)-methyl]-2-phenyl-acetamide;

2-[1-(3,4-Dimethoxy-benzyl)-8-hydroxy-7-methoxy-1,3,4,5-tetrahydro-benzo[c]azepin-2-yl]-N-indan-1-yl-acetamide;

2-[8-Benzyloxy-1-(3,4-dimethoxy-benzyl)-7-methoxy-1,3,4,5-tetrahydro-benzo[c]azepin-2-yl]-N-indan-1-yl-acetamide;

3-{2-[1-(3,4-Dimethoxy-benzyl)-7,8-dimethoxy-1,3,4,5-tetrahydro-benzo[c]azepin-2-yl]-2-phenyl-acetylamino}-propionic acid methyl ester;

N-(1H-Benzoimidazol-2-ylmethyl)-2-[1-(3,4-dimethoxy-benzyl)-7,8-dimethoxy-1,3,4,5-tetrahydro-benzo[c]azepin-2-yl]-2-phenyl-acetamide;

3-{2-[1-(3,4-Dimethoxy-benzyl)-7,8-dimethoxy-1,3,4,5-tetrahydro-benzo[c]azepin-2-yl]-2-phenyl-acetylamino}-N,N-dimethyl-propionamide;

3-{2-[1-(3,4-Dimethoxy-benzyl)-7,8-dimethoxy-1,3,4,5-tetrahydro-benzo[c]azepin-2-yl]-2-phenyl-acetylamino}-N-ethyl-N-methyl-propionamide;

2-[1-(3,4-Dimethoxy-benzyl)-7,8-dimethoxy-1,3,4,5-tetrahydro-benzo[c]azepin-2-yl]-N-isoxazol-5-ylmethyl-2-phenyl-acetamide;

2-[1-(3,4-Dimethoxy-benzyl)-7,8-dimethoxy-1,3,4,5-tetrahydro-benzo[c]azepin-2-yl]-N-(1H-indol-3-ylmethyl)-2-phenyl-acetamide;

2-[1-(3,4-Dimethoxy-benzyl)-7,8-dimethoxy-1,3,4,5-tetrahydro-benzo[c]azepin-2-yl]-N-isoquinolin-1-ylmethyl-2-phenyl-acetamide;

N-Cyanomethyl-2-[1-(3,4-dimethoxy-benzyl)-7,8-dimethoxy-1,3,4,5-tetrahydro-benzo[c]azepin-2-yl]-2-phenyl-acetamide;

N-(2-Acetylamino-ethyl)-2-[1-(3,4-dimethoxy-benzyl)-7,8-dimethoxy-1,3,4,5-tetrahydro-benzo[c]azepin-2-yl]-2-phenyl-acetamide;

2-[1-(3,4-Dimethoxy-benzyl)-7,8-dimethoxy-1,3,4,5-tetrahydro-benzo[c]azepin-2-yl]-2-phenyl-N-(2,2,2-trifluoro-ethyl)-acetamide;

2-[1-(3,4-Dimethoxy-benzyl)-7,8-dimethoxy-1,3,4,5-tetrahydro-benzo[c]azepin-2-yl]-N-(2-methylsulfanyl-ethyl)-2-phenyl-acetamide;

2-[1-(3,4-Dimethoxy-benzyl)-7,8-dimethoxy-1,3,4,5-tetrahydro-benzo[c]azepin-2-yl]-2-phenyl-N-quinolin-2-ylmethyl-acetamide;

N-(2-Cyano-ethyl)-2-[1-(3,4-dimethoxy-benzyl)-7,8-dimethoxy-1,3,4,5-tetrahydro-benzo[c]azepin-2-yl]-2-phenyl-acetamide;

2-[1-(3,4-Dimethoxy-benzyl)-7,8-dimethoxy-1,3,4,5-tetrahydro-benzo[c]azepin-2-yl]-N-(3-methoxy-propyl)-2-phenyl-acetamide;

2-[1-(3,4-Dimethoxy-benzyl)-7,8-dimethoxy-1,3,4,5-tetrahydro-benzo[c]azepin-2-yl]-N-(3-ethoxy-propyl)-2-phenyl-acetamide;

2-[1-(3,4-Dimethoxy-benzyl)-7,8-dimethoxy-1,3,4,5-tetrahydro-benzo[c]azepin-2-yl]-2-phenyl-acetamide;

2-[1-(3,4-Dimethoxy-benzyl)-7,8-dimethoxy-1,3,4,5-tetrahydro-benzo[c]azepin-2-yl]-2-phenyl-N-pyrazin-2-ylmethyl-acetamide;

2-[1-(3,4-Dimethoxy-benzyl)-7,8-dimethoxy-1,3,4,5-tetrahydro-benzo[c]azepin-2-yl]-2-phenyl-N-prop-2-ynyl-acetamide;

N-tert-Butyl-2-[1-(3,4-dimethoxy-benzyl)-7,8-dimethoxy-1,3,4,5-tetrahydro-benzo[c]azepin-2-yl]-2-phenyl-acetamide;

2-[1-(3,4-Dimethoxy-benzyl)-7,8-dimethoxy-1,3,4,5-tetrahydro-benzo[c]azepin-2-yl]-N-(3-methyl-butyl)-2-phenyl-acetamide;

2-[1-(3,4-Dimethoxy-benzyl)-7,8-dimethoxy-1,3,4,5-tetrahydro-benzo[c]azepin-2-yl]-N-(3,3-dimethyl-butyl)-2-phenyl-acetamide;

2-[1-(3,4-Dimethoxy-benzyl)-7,8-dimethoxy-1,3,4,5-tetrahydro-benzo[c]azepin-2-yl]-N-(1-ethyl-propyl)-2-phenyl-acetamide;

2-[1-(3,4-Dimethoxy-benzyl)-7,8-dimethoxy-1,3,4,5-tetrahydro-benzo[c]azepin-2-yl]-N-(2-ethylsulfanyl-ethyl)-2-phenyl-acetamide;

2-[1-(3,4-Dimethoxy-benzyl)-7,8-dimethoxy-1,3,4,5-tetrahydro-benzo[c]azepin-2-yl]-N-(2-hydroxy-ethyl)-2-phenyl-acetamide;

2-[1-(3,4-Dimethoxy-benzyl)-7,8-dinlethoxy-1,3,4,5-tetrahydro-benzo[c]azepin-2-yl]-N-(3-hydroxy-propyl)-2-phenyl-acetamide;

2-[8-Allyloxy-[l]1-(3,4-dimethoxy-benzyl)-7-methoxy-1,3,4,5-tetrahydro-benzo[c]azepin-2-yl]-N-indan-1-yl-acetamide;

2-[1-(3,4-Dimethoxy-benzyl)-7-methoxy-8-propoxy-1,3,4,5-tetrahydro-benzo[c]azepin-2-yl]-N-indan-1-yl-acetamide;

2-[1-(3,4-Dimethoxy-benzyl)-8-isopropoxy-7-methoxy-1,3,4,5-tetrahydro-benzo[c]azepin-2-yl]-N-indan-1-yl-acetamide;

2-[1-(S)-(3,4-Dimethoxy-benzyl)-7,8-dimethoxy-1,3,4,5-tetrahydro-benzo[c]azepin-2-yl]-N-indan-1-yl-acetamide; and 2-[1-(S)-(3,4-Dimethoxy-benzyl)-7,8-dimethoxy-1,3,4,5-tetrahydro-benzo[c]azepin-2-yl]-N-indan-2-yl-acetamide.

5. The compound of claim 4 wherein said compound is 2-[1-(3,4-dimethoxy-benzyl)-7,8-dimethoxy-1,3,4,5-tetrahydro-benzocazepin-2-yl]-2-phenyl-N-prop-2-ynyl-acetamide.

* * * * *